US012778969B2

(12) United States Patent
Tran et al.

(10) Patent No.: US 12,778,969 B2
(45) **Date of Patent: *Nov. 3, 2026**

(54) LOW-SORBING GLYBURIDE FORMULATION AND METHODS

(71) Applicant: REMEDY PHARMACEUTICALS, INC., New York, NY (US)

(72) Inventors: Kenny K. Tran, Wakefield, MA (US); Deirdre Lowe, Salem, MA (US); Rupa Rishikesh Sawant, Wayland, MA (US); Haihong Chen, Acton, MA (US); Yiqing Lin, Lexington, MA (US)

(73) Assignee: REMEDY PHARMACEUTICALS, INC., New York, NY (US)

(*) Notice: Subject to any disclaimer, the term of this patent is extended or adjusted under 35 U.S.C. 154(b) by 1057 days.

This patent is subject to a terminal disclaimer.

(21) Appl. No.: 17/686,538

(22) Filed: Mar. 4, 2022

(65) Prior Publication Data

US 2022/0280537 A1 Sep. 8, 2022

Related U.S. Application Data

(60) Provisional application No. 63/156,533, filed on Mar. 4, 2021.

(51) Int. Cl.

| | |
|---|---|
| ***A61K 31/64*** | (2006.01) |
| ***A61K 9/00*** | (2006.01) |
| ***A61K 9/19*** | (2006.01) |
| ***A61K 47/18*** | (2017.01) |
| ***A61K 47/26*** | (2006.01) |

(52) U.S. Cl.

CPC ............ *A61K 31/64* (2013.01); *A61K 9/0019* (2013.01); *A61K 9/19* (2013.01); *A61K 47/18* (2013.01); *A61K 47/26* (2013.01)

(58) Field of Classification Search

CPC ........ A61K 31/64; A61K 9/0019; A61K 9/19; A61K 47/18; A61K 47/26

See application file for complete search history.

(56) References Cited

U.S. PATENT DOCUMENTS

| | | | | |
|---|---|---|---|---|
| 5,773,029 | A | 6/1998 | Chiesi et al. | |
| 7,803,786 | B2 | 9/2010 | McMahon | |
| 8,277,845 | B2 | 10/2012 | Jacobson | |
| 10,441,556 | B2 | 10/2019 | Jacobson et al. | |
| 10,688,111 | B2 * | 6/2020 | Jacobson | A61P 3/10 |
| 10,758,503 | B2 | 9/2020 | Jacobson et al. | |
| 2011/0034560 | A1 * | 2/2011 | Jacobson | A61K 47/26 514/593 |
| 2015/0051289 | A1 | 2/2015 | Polak et al. | |
| 2020/0022993 | A1 | 1/2020 | Zhong et al. | |

FOREIGN PATENT DOCUMENTS

| | | | | |
|---|---|---|---|---|
| CN | 105878194 | A | 8/2016 | |
| CN | 108553428 | A | 9/2018 | |
| EP | 1250321 | A1 | 10/2002 | |
| WO | WO-03063825 | A1 * | 8/2003 | A61K 9/0004 |
| WO | 2016138473 | A1 | 9/2016 | |
| WO | WO-2018108111 | A1 * | 6/2018 | A61K 31/64 |
| WO | 2020223436 | A1 | 11/2020 | |

OTHER PUBLICATIONS

Hasim "Efficacy and safety of isotonic and hypotonic intravenous maintenance fluids in hospitalised children" Children 2021 8 785 (Year: 2021).*

Jamal "Solution behaviour and sweetness response of D-Mannitol at different temperatures" Food Chemistry 2014 153 140-144 (Year: 2014).*

Lobenberg "Dissolution Testing as a Prognostic Tool for Oral Drug Absorption: Dissolution Behavior of Glibenclamide" Pharm Res 2000 17 439-444 (Year: 2000).*

"Mannitol", Handbook of Pharmaceutical Excipients 6e, Crowe 2009, p. 424 (Year: 2009).*

Suresh et al. "Polymorphism, isostructurality and physicochemical properties of glibenclamide salts†" CrystEngComm, 2017, 19, 918-929 (Year: 2017).*

Berge et al., "Pharmaceutical Salts" Journal of Pharmaceutical Sciences 1977 66 1 1-14 (Year: 1977).*

Hasim et al., "Efficacy and safety of isotonic and hypotonic intravenous maintenance fluids in hospitalised children" Children 2021, 8, 785 (Year: 2021).*

Tromethamine, The Merck Index Online, May 3, 2025, Retrieved from merckindex.rsc.org (Year: 2025).*

Diethanolamine (D8885) [online], MilliporeSigma, 2010 [retrived on May 5, 2025], Retrieved from the internet, https://www.sigmaaldrich.com/US/en/product/sigma/31589 (Year: 2025).*

Madgulkar et al. "Sugars as solid dispersion carrier to improve solubility and dissolution of the BCS class II drug: clotrimazole" Drug Dev Ind Pharm, 2016, 42, 1, 28-38 (Year: 2016).*

Wei et al. Physicochemical characterization of five glyburide powders: A BCS based approach to predict oral absorption Eur J Pharm Biopham 2008 69 1046-1056 (Year: 2008).*

Neils et al. "The pKa of Water and the Fundamental Laws Describing Solution Equilibria: An Appeal for a Consistent Thermodynamic Pedagogy" Helv. Chim. Acta 2024, 107, e202400103 (Year: 2024).*

International Search Report and Written Opinion issued in PCT/US2022/018821 dated Sep. 26, 2022, 14 pages.

Non-Final Office Action for co-pending U.S. Appl. No. 18/635,765, dated Sep. 25, 2024. (20 pages).

(Continued)

*Primary Examiner* — Sahana S Kaup
*Assistant Examiner* — Toriana N. Vigil
(74) *Attorney, Agent, or Firm* — ROTHWELL, FIGG, ERNST & MANBECK, P.C.

(57) ABSTRACT

Methods and formulations for minimizing or avoiding the sorption of glyburide to surfaces of delivery tubing, filters, bags, and other containers and materials, thereby storing and delivering a more stable product, delivering a predictable and accurate dose of glyburide, while minimizing impurities, avoiding drug waste, reducing cost, and significantly reducing the amount of dosing solution that must be infused into the patient.

51 Claims, 14 Drawing Sheets

(56) References Cited

OTHER PUBLICATIONS

Figueroa-Valverde, et al.; "Glibenclamide-Pregnenolone Derivative Has Greater Hypoglycemic Effects and Biodistribution Than Glibenclamide-OH In Alloxan-Rats"; Biomedical Pap Med Fac Univ Palacky Olomouc Czech Repub, Jun. 2012, vol. 156, No. 2; pp. 122-127.
Berge, et al., "Pharmaceutical Salts"; Journal of Pharmaceutical Sciences, vol. 66, No. 1, Jan. 1977, pp. 1-19.
Vial2Bag AdvancedTM 20mm Admixture Device: Instruction for Use; issued Oct. 27, 2020; Ref. No. 1090209 Rev. 1.0; 510(k) Ref. No. K210415; http://www.publicweb.novanthealth.org/Vial2Bag/Vial2Bag_Advanced_20mm.pdf; retrieved via web on Sep. 12, 2024.
Non-Final Office Action for co-pending U.S. Appl. No. 19/191,890, dated Oct. 17, 2025. (18 pages).
Non-final Office Action for corresponding U.S. Appl. No. 19/341,379 dated May 11, 2026. (15 pages).
L. Figueroa-Valverde, et al.; "Synthesis of Glibenclamide-pregnenolone conjugate and its relationship with physico-chemical descriptors log P, Π, Rm, Vm, Pc, and St"; Asian Journal of Chemistry, 2011; vol. 23; No. 9; pp. 3999-4002.
Notice of Reasons for Rejection for corresponding Japanese Application No. 2023-553299 mailed Mar. 11, 2026. (13 pages).
Final Office Action for corresponding U.S. Appl. No. 19/341,379 dated Aug. 17, 2026. (16 pages).

* cited by examiner

LOW-SORBING GLYBURIDE FORMULATION AND METHODS

CROSS REFERENCE TO RELATED APPLICATION

This application claims the benefit of provisional application 63/156,533 filed Mar. 4, 2021, the disclosure of which is incorporated herein in its entirety by reference.

FIELD OF THE DISCLOSURE

This disclosure relates to the field of medical treatment methods, including intravenous methods of administration of drugs to a subject.

BACKGROUND

Glyburide (also known as, e.g., glibenclamide) is a sulfonylurea drug used in treating diabetes. The systematic name of glyburide is 5-chloro-N-(4-[N-(cyclohexylcarbamoyl) sulfamoyl]phenethyl)-2-methoxybenzamide. Glyburide preferentially binds to and affects the sulfonylurea receptor 1 (SUR1) but at higher concentrations also binds to and affects the sulfonylurea receptor 2 (SUR2).

Glyburide has been suggested as a therapy for various disorders including but not limited to Large Hemispherical Infarction (LHI), acute stroke (ischemic and hemorrhagic), traumatic brain injury (TBI), spinal cord injury (SCI), myocardial infarction (MI), brain contusion (BC), edema, traumatic brain injury, subarachnoid hemorrhage, spinal cord injury, shock (including hemorrhagic shock), organ ischemia, ventricular arrhythmias, to prevent CNS edema, reduce mortality and preserve neurological function.

Glibenclamide solubility in various solutions has been reported, and is typically reported as being very poorly soluble in buffered aqueous solutions. For example, the solubility of glibenclamide in buffered aqueous solutions has been reported by Glomme et al. (Glomme A, Marz J, Dressman J B. Comparison of a miniaturized shake-flask solubility method with automated potentiometric acid/base titrations and calculated solubilities. J Pharm Sci. 2005 January; 94(1):1-16). The buffered aqueous solution was made with distilled water to form a potassium chloride (220 mM) solution buffered with potassium phosphate (29 mM), and the pH adjusted to pH 5, 6, or 7 with sodium hydroxide. These solutions had osmolarities of between about 280 to 310 milliOsmolar and had buffer capacities of about 10±2 milliEquvialents/L/pH. Glomme et al. report that glibenclamide is only sparingly soluble in such solutions, with extremely low solubilities at pH 2, 3, 5, 6, and 7, and relatively greater (although still very low) solubilities at pH 8, 9 and 11.8. These solubilities are shown in Table 1:

TABLE 1

Solubility of glibenclamide at 37° C. (aqueous)

| pH | Solubility (mg/ml) |
|---|---|
| 2 | 0.00007 |
| 3 | 0.00006 |
| 5 | 0.0001 |
| 6 | 0.00062 |
| 7 | 0.00562 |
| 8 | 0.0512 |
| 9 | 0.0986 |
| 11.8 | 0.5316 |

Similarly, low glibenclamide solubilities in aqueous solutions were reported by Kaiser et al. (Kaiser D G, Forist, A A. A review of Glibenclamide Metabolism in Man and Laboratory Animals. Physical and Analytical Chemistry Research, The Upjohn Company; 1975), with solubilities of below 1 mg/mL at all measured pH values from pH 4 to pH 9. Glibenclamide was dissolved in Britton-Robinson buffer. (Britton-Robinson buffer is an aqueous buffer solution including phosphoric acid, acetic acid and boric acid, with the pH adjusted with sodium hydroxide.) These solubilities are reported in Table 2.

TABLE 2

Solubility of glibenclamide at 27° C. (aqueous)

| pH | Solubility (mg/ml) |
|---|---|
| 4 | 0.004 |
| 6 | 0.005 |
| 7 | 0.011 |
| 8 | 0.080 |
| 9 | 0.600 |

Applicants have discovered that the concentration of glyburide is reduced in glyburide solutions placed in various types of pharmaceutical containers due to various processes including instability, degradation, and sorption of glyburide to such containers. Glyburide is practically insoluble within the typical pH range for pharmaceutically acceptable infusion solutions (pH 5-9), which presents challenges for obtaining stable glyburide formulations that can be dosed to patients over time. It is also necessary and critical to control the stability of the stored glyburide formulation and the diluted dosing solution (e.g., after ~100-fold dilution of the stored glyburide formulation) for infusion.

An additional challenge is that diluted solutions of glyburide readily bind to plastics such as polyvinylchoride (PVC) or polyurethane (PUR), materials that are commonly used in infusion components such as saline IV bags and administration sets. While in Phase 1-3 clinical trials in the United States, specialized infusion sets (low-sorbing, polyethylene-lined) have been used to address drug-material compatibility issues, this stopgap strategy is not practical for multiple reasons including that it is difficult to source the specialized infusion sets and glyburide is intended for use in an emergency-care setting and for indications where minimization in the time from the patient's last-know-normal to dosing is critical for efficacy (i.e. "time is brain"). The pace of neural circuitry loss in human ischemic stroke emphasizes the time urgency of care of patients suffering from stroke and brain injuries. For example, the typical patient loses 1.9 million neurons each minute in which stroke is untreated. Thus, added complexities in the handling and administration of intravenous glyburide (i.e. requirement for specialized infusion components) would delay patient dosing and adversely affect patient outcome. Moreover, use of commonly used materials would result in loss of significant amounts of the active pharmaceutical ingredient due to sorption, resulting in administration of an unknown and likely sub-therapeutic dose of the glyburide, again adversely affecting patient outcome. Moreover, it is unsafe to administer imprecise amounts of glyburide because glyburide is known to result in hypoglycemia. In administering intravenous glyburide formulations at therapeutic concentrations for treatment of stroke (LHI) or brain contusion, the inventors have found that about 40-50% of the glyburide is wasted due to, e.g., instability, sorption, and process problems.

Thus, there is a need in the field to produce glyburide formulations that prevent the concentration of glyburide from being reduced due to sorption of glyburide to surfaces of delivery tubing, filters, bags, catheters, syringes, infusion sets, extension sets, and other containers and materials that come into contact with the glyburide. There is a need in the field to produce glyburide formulations having higher stability at lower pHs. There is a need in the field to produce glyburide formulations with reduced generation of degradation products. There is a need in the field to produce glyburide formulations that require significantly less saline infusion fluids to administer a therapeutic dose intravenously. There is a need in the field to produce glyburide formulations that have improved storage stability.

SUMMARY OF THE INVENTION

The present disclosure includes formulations, kits, and methods for minimizing or avoiding the sorption of glyburide to surfaces of delivery tubing, filters, bags, and other containers and materials, thereby storing and delivering a more stable product, a predictable and accurate dose of the glyburide, while minimizing impurities, avoiding drug waste, reducing cost, and significantly reducing the amount of dosing solution (typically saline or a Ringer's solution) that must be infused into the patient.

In one aspect, the present disclosure includes formulation comprising: glyburide or a pharmaceutically acceptable salt thereof; a buffering agent; a base; and a sugar alcohol, wherein the formulation has a pH outside of the buffering capacity of the buffering agent.

In one aspect, the present disclosure includes an infusion solution comprising 500 ml saline solution, 3 to 5 mg glyburide, 100-140 mg mannitol, 10-12 mg Tris, and pH 7.8 to 9.

In one aspect, the present disclosure includes a solution comprising 10-30 ml WFI, 3 to 5 mg glyburide, 100-140 mg mannitol, 10-12 mg Tris, and pH 9 to 11, e.g., 9.4 to 10.

In one aspect, the present disclosure includes a method of making a glyburide formulation that has less than 1 wt. % loss of glyburide concentration (w/v) due to sorption to a polymeric container over the course of an infusion period comprising combining glyburide with a buffering agent having a pKa of 7.7 to 9.2, a sugar alcohol, and a base having a pKb of 0.1 to 1.5 in a molar ratio between the base and the glyburide of 5.0 to 6.7:1.

In some aspects, the present disclosure includes reconstitution the formulations of the present disclosure in a suitable diluent, e.g., saline or water for injection (WFI) such that the reconstituted formulation has a concentration of 4 to 60 mM, 5 to 50 mM, 6 to 40 mM, 7 to 30 mM, 8 to 25 mM, 9 to 23 mM, 10 to 21 mM, 11 mM, 12 mM, 13 mM, 14 mM, 15 mM, 16 mM, 17 mM, 18 mM, 19 mM, or 20 mM of the buffering agent.

In some aspects, the present disclosure includes diluting the formulations of the present disclosure in a saline solution, wherein the formulation has a pH of 7.8 to 9.

In some aspects, the present disclosure includes diluting the formulation in a saline solution, wherein the formulation has a pH that does not vary by more than 0.2 pH units during an infusion period of at least 24 hours.

In some aspects, the present disclosure includes formulations and methods having high storage stability, e.g., storage stability properties such that, upon storage for 6 months at 25° C./60% RH, has less than 0.2% degradation products, upon storage for 6 months at 40° C./75% RH, has less than 0.4% degradation products, and/or upon storage for 7 days at 70° C./75% RH, has less than 1.0% degradation products.

In some aspects, the present disclosure includes a method of increasing the solubility of a glyburide formulation in a saline infusion solution, comprising combining glyburide or a pharmaceutically acceptable salt thereof with: a buffering agent; a base; and a sugar alcohol, wherein the formulation has a pH outside of the buffering capacity of the buffering agent at 4° C., 20° C., or 25° C., to form a solubilized glyburide formulation having a glyburide solubility of 15 μg/ml in said saline infusion solution, wherein the glyburide formulation in the saline infusion solution has a pH of 7.8 to 9.

In some aspects, the present disclosure includes a method of minimizing the volume of saline infusion solution necessary for infusing a glyburide formulation into a human for 24 hours, comprising combining 3 to 5 mg glyburide or a pharmaceutically acceptable salt thereof with a buffering agent; a base; and a sugar alcohol, wherein the formulation has a pH outside of the buffering capacity of the buffering agent, wherein the glyburide formulation in the saline infusion solution has a pH of 7.8 to 9, and wherein the volume of the saline infusion solution used to infuse 3 to 5 mg glyburide or a pharmaceutically acceptable salt thereof to the human is about 500 ml.

In some aspects, the present disclosure includes a method of increasing the storage stability of a glyburide formulation comprising combining glyburide or a pharmaceutically acceptable salt thereof with a buffering agent; a base; and a sugar alcohol, wherein the formulation has a pH outside of the buffering capacity of the buffering agent, to form a stabilized glibenclamide formulation, wherein said stabilized glibenclamide formulation, after storage for at least 6 months at 25° C./60% RH, and has less than 0.2% degradation products upon storage for 6 months at 25° C./60% RH.

In some aspects, the present disclosure includes a compound having the structure:

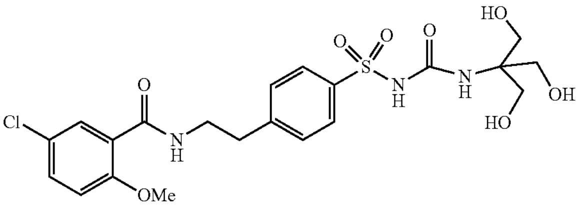 [SMILES: COc1ccc(Cl)cc1C(=O)NCCc1ccc(S(=O)(=O)NC(=O)NC(CO)(CO)CO)cc1]

and formulations containing the compound including any active metabolite, salt, ester, hydrate, solvate, crystalline form, co-crystalline form, amorphous form, pro-drug (including ester pro-drug) form, racemate, polymorph, chelate, tautomer, stereoisomer, or optically active form thereof.

In some aspects, the present disclosure includes a composition of the present disclosure further comprising a compound having the structure:

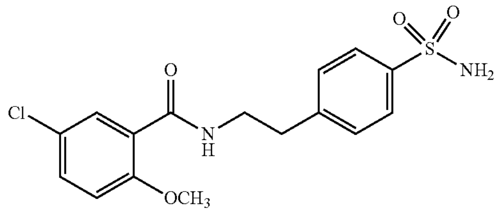 [SMILES: COc1ccc(Cl)cc1C(=O)NCCc1ccc(S(N)(=O)=O)cc1]

including any active metabolite, salt, ester, hydrate, solvate, crystalline form, co-crystalline form, amorphous form, pro-drug (including ester pro-drug) form, racemate, polymorph, chelate, tautomer, stereoisomer, or optically active form thereof.

In some aspects, the present disclosure includes a compound having the structure:

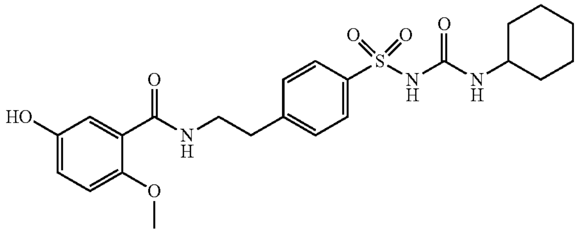 [SMILES: COc1ccc(O)cc1C(=O)NCCc1ccc(S(=O)(=O)NC(=O)NC2CCCCC2)cc1]

and formulations containing the compound including any active metabolite, salt, ester, hydrate, solvate, crystalline form, co-crystalline form, amorphous form, pro-drug (including ester pro-drug) form, racemate, polymorph, chelate, tautomer, stereoisomer, or optically active form thereof.

In some aspects, the present disclosure includes a composition of the present disclosure further comprising a compound having the structure:

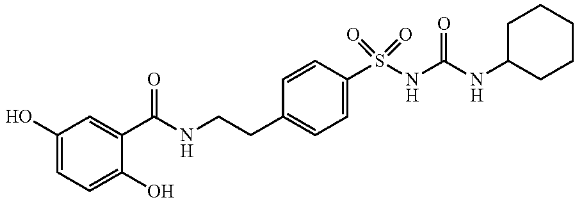 [SMILES: O=C(NC1CCCCC1)NS(=O)(=O)c1ccc(CCNC(=O)c2cc(O)ccc2O)cc1]

including any active metabolite, salt, ester, hydrate, solvate, crystalline form, co-crystalline form, amorphous form, pro-drug (including ester pro-drug) form, racemate, polymorph, chelate, tautomer, stereoisomer, or optically active form thereof.

In some aspects, the present disclosure includes a compound having the structure:

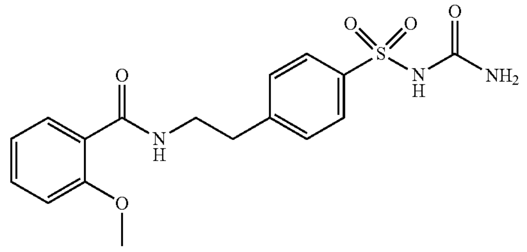 [SMILES: COc1ccccc1C(=O)NCCc1ccc(S(=O)(=O)NC(N)=O)cc1]

and formulations containing the compound including any active metabolite, salt, ester, hydrate, solvate, crystalline form, co-crystalline form, amorphous form, pro-drug (including ester pro-drug) form, racemate, polymorph, chelate, tautomer, stereoisomer, or optically active form thereof.

In some aspects, the present disclosure includes a compound having the structure:

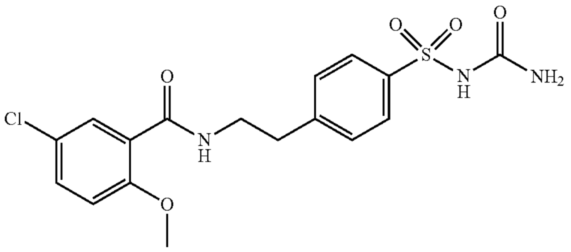 [SMILES: COc1ccc(Cl)cc1C(=O)NCCc1ccc(S(=O)(=O)NC(N)=O)cc1]

and formulations containing the compound including any active metabolite, salt, ester, hydrate, solvate, crystalline form, co-crystalline form, amorphous form, pro-drug (including ester pro-drug) form, racemate, polymorph, chelate, tautomer, stereoisomer, or optically active form thereof.

In some aspects, the present disclosure includes a compound having the structure:

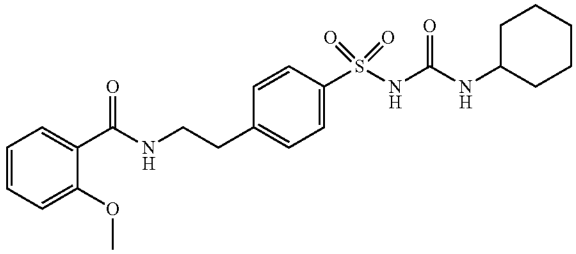 [SMILES: COc1ccccc1C(=O)NCCc1ccc(S(=O)(=O)NC(=O)NC2CCCCC2)cc1]

and formulations containing the compound including any active metabolite, salt, ester, hydrate, solvate, crystalline form, co-crystalline form, amorphous form, pro-drug (including ester pro-drug) form, racemate, polymorph, chelate, tautomer, stereoisomer, or optically active form thereof.

In some aspects, the present disclosure includes a kit comprising a first container containing a lyophilized formulation comprising: glyburide or a pharmaceutically acceptable salt thereof; a base; a sugar alcohol; and a buffering agent, and an admixture device configured to reconstitute and transfer the lyophilized formulation between the first container and a second container prior to administration, wherein the lyophilized formulation, when reconstituted in the second container, has a pH outside of the buffering capacity of the aqueous buffer.

In some aspects, the present disclosure includes a method of treating a patient suffering from a stroke, hemorrhage, neuronal cell swelling, traumatic brain injury, spinal cord injury, organ ischemia, acute coronary syndrome, myocardial infarction, sepsis, brain contusion, shock, ischemia, or a ventricular arrhythmia.

In some aspects, the present disclosure includes a reconstituted formulation comprising WFI and a lyophilized formulation comprising glyburide or a pharmaceutically acceptable salt thereof; a buffering agent; a base; and a sugar alcohol, wherein the formulation has a pH outside of the buffering capacity of the buffering agent, wherein the reconstituted formulation comprises at least 95, 96, 97, 98, or 99% of the amount of glyburide or pharmaceutically acceptable salt thereof in the lyophilized formulation.

In some aspects, the present disclosure includes an infusion formulation comprising saline infusion solution and an aqueous or lyophilized formulation comprising: glyburide or a pharmaceutically acceptable salt thereof; a buffering agent; a base; and a sugar alcohol, wherein the formulation has a pH outside of the buffering capacity of the buffering agent, wherein the infusion solution comprises at least 95, 96, 97, 98, or 99% of the amount of glyburide or pharmaceutically acceptable salt thereof in the lyophilized formulation.

In some aspects, the present disclosure includes a method for controlling the pH of a glyburide solution diluted in a saline infusion solution in a pH range of 8 to 9 over the course of a 24 hour infusion, comprising combining: glyburide or a pharmaceutically acceptable salt thereof; a buffering agent; a base; and a sugar alcohol, wherein the formulation has a pH outside of the buffering capacity of the buffering agent to form a stabilized and soluble glyburide formulation, diluting the stabilized and soluble glyburide formulation in the saline infusion solution, and infusing the diluted formulation into a patient, wherein the pH of the diluted formulation is 7.8 to 9 and the pH of the diluted formulation does not change by more than 0.2 pH units over the course of the 24 hour infusion.

In some aspects, the present disclosure includes a method for reducing the infusion rate of a glyburide solution diluted in a saline infusion solution over the course of a 24 hour infusion, comprising combining: 3 to 5 mg glyburide or a pharmaceutically acceptable salt thereof; a buffering agent; a base; and a sugar alcohol, wherein the formulation has a pH outside of the buffering capacity of the buffering agent, to form a stabilized and soluble glyburide formulation, diluting the stabilized and soluble glyburide formulation in the saline infusion solution, and infusing the diluted formulation into a patient at a rate of less than 16 ml/hour for 24 hours.

In some aspects, the present disclosure includes a compounding process comprising sequentially adding glyburide to mannitol to form a first mixture, then adding Tris-base to the first mixture to form a second mixture, then adding Tris-HCl to the second mixture to form a third mixture, then adding a first amount of NaOH to the third mixture to form a fourth mixture comprising glyburide dissolved and solubilized therein at 1 mg/ml and below pH of 10.0, and then adding a second amount of NaOH to the fourth mixture to form a final formulation having a comprising glyburide dissolved and solubilized therein at 1 mg/ml and having a pH of 10.4±0.4.

Other features and characteristics of the subject matter of this disclosure, as well as the methods of operation, functions of related elements of structure and the combination of parts, and economies of manufacture, will become more apparent upon consideration of the following description and the appended claims, all of which form a part of this specification.

BRIEF DESCRIPTION OF THE DRAWINGS

FIG. 10A (top and bottom) shows the minimum and maximum pH of final dosing solution based on a vial fill of 6 ml. FIG. 10B (top and bottom) shows the minimum and maximum pH of final dosing solution based on a vial fill of 4 ml.

DETAILED DESCRIPTION

Figure 1:
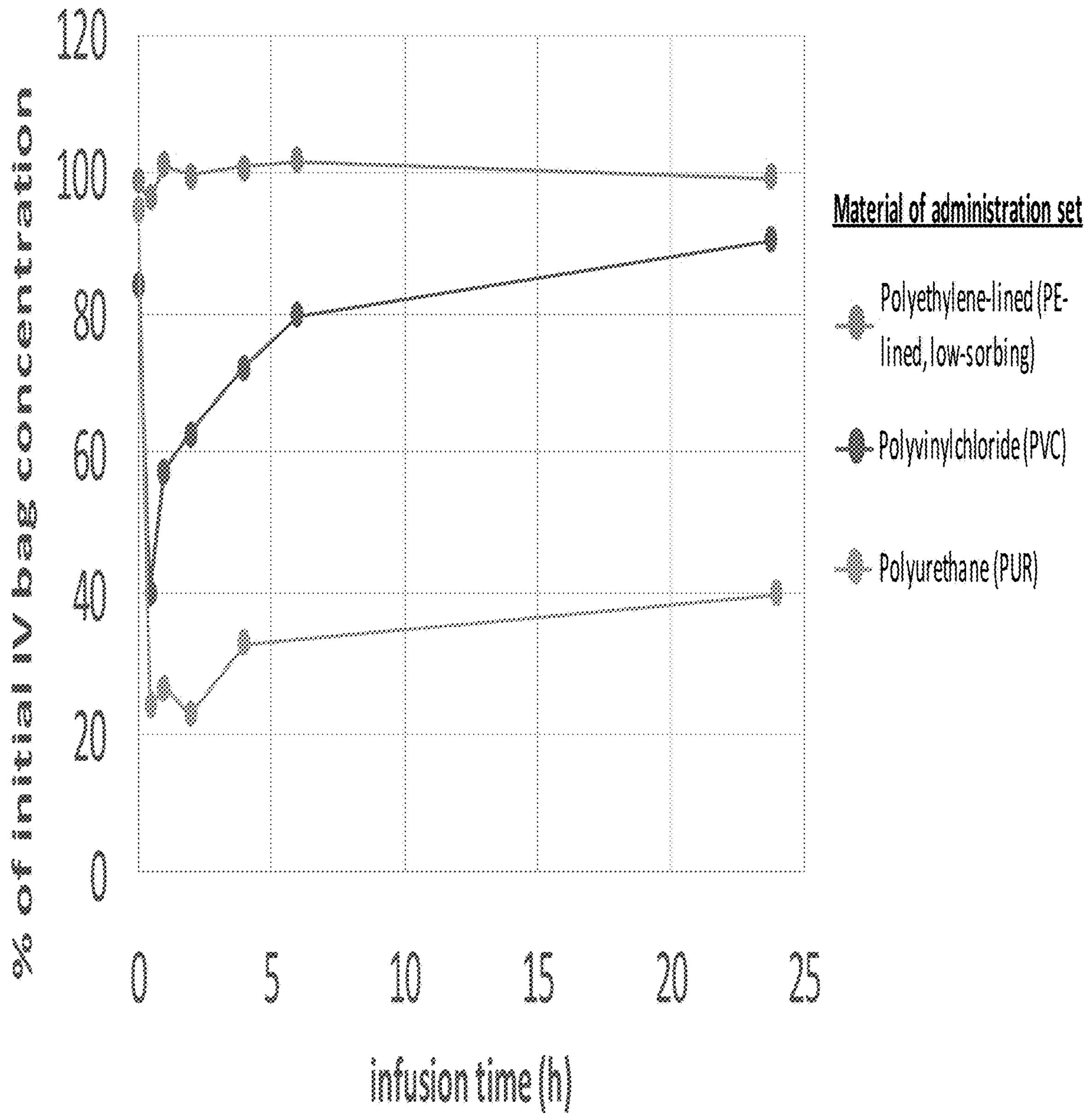
FIG. 1 shows the sorption of prior art glyburide intravenous formulations to medical materials.

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or embodiments so described.

The singular forms "a," "an," and "the" include plural referents unless the context clearly dictates otherwise.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of," as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value. Numerical quantities given are approximate, meaning that the term "around," "about" or "approximately" can be inferred if not expressly stated.

As used herein, the term "pharmaceutically acceptable" refers to solvents, co-solvents, surfactants, carriers, diluents, excipients, buffers, salts, and/or other components that are compatible with the other ingredients of the formulation and are not deleterious to the recipient thereof. In some aspects, the glyburide formulation of the present disclosure may include one or more sugar alcohols including but not limited to include allitol, arabitol, dextrose, dulcitol, erythritol, galactitol, glycol, glycerol, iditol, isomalt, lactitol, maltitol, mannitol, sorbitol, threitol, xylitol, and combinations thereof.

As used herein, the term "lyophilized" and grammatical variants thereof refers to dried materials, such as powders, from liquids containing solids or dissolved materials by freeze-drying (freezing a liquid containing dissolved or suspended material, and drying while frozen by sublimation) to provide a dry solid containing the dissolved or suspended material in solid form. Typically, aqueous solutions are used in lyophilization, although mixed aqueous/solvent solutions, and other liquid solutions, may be used. For example, a biological material may be lyophilized from a solution or suspension in which it is mixed with protective agents. Such a solution or suspension may then be frozen, and subsequently dehydrated by sublimation. Sublimation may optionally be followed by further drying steps. Typically, lyophilization methods include freeze-drying a liquid solution or suspension to provide a dry residue containing a high concentration of the dissolved or suspended compounds. In some cases, the solid provided by lyophilization may be or include a salt. Lyophilization processes provide solids, such as powders, dried films, or cakes. Small particles may be obtained, if desired, from such powders, films, or cakes by procedures such as grinding or flaking.

The methods and formulations provided herein provide pharmaceutically acceptable glyburide formulations, including concentrated solutions, diluted solutions, and lyophilized formulations, that solve the sorption, degradation, instability, and low solubility problems associated with prior art pharmaceutical formulations glyburide.

Examples of suitable pharmaceutically acceptable diluents such as WFI (water for injection) and solutions containing isotonic saline are known in the art. Pharmaceutically acceptable aqueous solutions include Ringer's solution, Hartmann's solution, 0.9% saline, 0.45% N saline, WFI (water for injection), D5W (5% dextrose in water), phosphate-buffered saline (PBS), and a dextrose/saline solution (D2.5W (i.e., 2.5% dextrose in water) and 0.45% N saline).

As used herein, "Ringer's solution" refers to a pharmaceutically acceptable buffered saline solution having sodium chloride, potassium chloride, and calcium chloride salts.

As used herein, "Hartmann's solution" refers to a lactated Ringer's solution. A typical Hartmann's solution includes 131 mM sodium, 5 mM potassium, 2 mM calcium, 11 mM chloride, and 29 mM lactate (sodium chloride 0.6%, sodium lactate 0.25%, potassium chloride 0.04%, calcium chloride 0.027%).

As used herein, pharmaceutically acceptable saline solution is a solution suitable for administration to a patient that includes water and sodium chloride, and may optionally contain buffers, preservatives, or other components, typically in small amounts. For example, pharmaceutically acceptable saline solutions include 0.9% saline (9 g NaCl in 100 ml distilled, filtered water, containing 150 mM sodium and 150 mM chloride) and saline solutions having 154 mM sodium and 154 mM chloride.

Generally herein, the term "or" includes "and/or."

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, elements, excipients, ingredients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of method steps, active agents, kits, or compositions described with respect to a formulation or method of treating a certain subject is intended to and does find direct support for embodiments related to compositions, formulations, and methods described in any other part of this disclosure, even if those method steps, active agents, kits, or compositions are not re-listed in the context or section of that embodiment or aspect.

The inventors have found that glyburide in conventional intravenous glyburide formulations readily and extensively binds to polymeric containers, e.g., containing polyvinyl chloride (PVC) and polyurethane (PUR) infusion sets. See FIG. 1. While use of low-sorbing polyethylene-lined infusion sets minimize the sorption, such specialized infusion sets are not practical for multiple reasons including that it is difficult to source such specialized infusion sets and intravenous glyburide is intended for use in an emergency-care setting and for indications where minimization in the time from the patient's last-know-normal to dosing is critical for efficacy (i.e. "time is brain"). Thus, presenting additional complexities in the handling and administration of intravenous glyburide, i.e., requiring strict use of specialized infusion components in emergency settings, would delay patient dosing and adversely affect patient outcome. Moreover, use of commonly used materials with prior art intravenous glyburide formulations would result in loss of significant amounts of the active pharmaceutical ingredient due to sorption, resulting in administration of an unknown and likely sub-therapeutic dose of the glyburide. In addition, use of commonly used materials with prior art intravenous glyburide formulations results in instability and degradation leading to unacceptable quality drug product. Further, it is unsafe to administer unknown amounts of glyburide or to attempt to increase the volume of drug to administer because administering glyburide in higher doses (e.g., at a rate greater than an average rate of 0.25 mg/hour (6 mg/day)) can result in hypoglycemia. As shown in FIG. 1, there are significant and unpredictable changes amount of the glyburide in prior art intravenous glyburide formulations that bind to commonly used infusion sets over the course of the infusion period. Further, it is not desirable to implement flushing procedures, which can be complex, time-consuming, imprecise, wasteful, and risk contamination. Moreover, the inventors have found that glyburide in prior art intravenous glyburide formulations readily and extensively binds to all filter components (data not shown). Thus, it is necessary to provide new intravenous glyburide formulations that avoid binding to commonly used infusion sets and filter materials and allow healthcare providers to treat patients with a precise dose within the appropriate dosing window (as close to immediately after a stroke, infarction, injury, etc.) using commonly used medical supplies, while avoiding complication, avoiding wasted drug, and reducing the amount of infusion fluid administered to patients.

In a first aspect, the present disclosure provides a formulation containing a stable, therapeutic dose of glyburide that has less than 8, 7, 6, 5, 4, 3, 2, 1, 0.5, 0.2, 0.1, 0.05, 0.01% loss of glyburide concentration (w/v) due to sorption to a polymeric container, e.g., containing polyvinyl chloride (PVC), polyurethane (PUR), polypropylene, polyamide, polystyrene, polyethylene terephthalate (PET), polycarbonate (PC), acrylonitrile butadiene (ABS), polybutadiene, polyolefin, ethylene vinyl acetate, polyetheretherketone (PEEK), and mixtures, combinations, and copolymers thereof.

In a second aspect, the present disclosure provides a formulation containing a stable, therapeutic dose of glyburide that has less than 8, 7, 6, 5, 4, 3, 2, 1, 0.5, 0.2, 0.1, 0.05, 0.01% loss of glyburide concentration (w/v) due to sorption to in line filter materials.

In a third aspect, the present disclosure provides a method and formulation for controlling the pH of a glyburide solution in a narrow desired range both before and after dilution in an infusion fluid.

In a fourth aspect, the present disclosure provides a method and formulation for minimizing or avoiding degradation products from forming in a stored glyburide solution.

In a fifth aspect, the present disclosure provides a method and formulation for reducing the infusion rate, reducing drug wastage, and reducing saline intake into a subject being treated with intravenous glyburide.

In a sixth aspect, the present disclosure provides a method and formulation for maintaining a sufficiently high concentration of glyburide in solution during formulation compounding that can enable filling into appropriately-sized container to achieve the therapeutic dose, e.g., 3-5 mg per day glyburide.

In a seventh aspect, the present disclosure provides a method and formulation for providing sufficient solubility, stability, and desired pH upon reconstitution to achieve a desired high concentration during drug preparation.

In an eighth aspect, the present disclosure provides a method and formulation for providing sufficient solubility, stability, and desired pH upon further dilution of the reconstituted glyburide formulation into infusion fluids (e.g., in saline bags at a concentration of 6-10 μg/ml) for dosing over a 3, 4, 6, 12, 24, 30, 36, 48, 72, 96, or 120 hour period.

In one aspect, the method and formulation of the present disclosure includes compounding a glyburide formulation including glyburide, a buffering agent, and a base as specified herein. In one aspect, the buffering agent has a pKa of 7.7 to 9.2, 7.8 to 9.1, 7.9 to 9.0, 8.0 to 8.9, 8.05 to 8.8, 8.1 to 8.7, or any specific pKa in the specified ranges. For example, and without limiting the foregoing disclosure, the buffering agent may be a Tris, a lysine, an arginine, an ethylenediamine, an imidazole, a 4-(2-Hydroxyethyl)morpholine, a triethanolamine, a glucamine, a deanol (dimethylaminoethanol), phosphate, phosphate-buffered saline (PBS) S) or a combination thereof. In one aspect, the buffering agent of the present disclosure has buffering capacity in a pH range of 7 to 9. In one aspect the Tris may be a combination of Tris-HCl and Tris-base. In one aspect, the lysine is lysine-HCl. In one aspect, the arginine is arginine-HC1.

In one aspect, the present disclosure includes methods and formulations comprising glyburide, a buffering agent, a base, and a sugar alcohol, wherein the formulation has a pH outside of the buffering capacity of the buffering agent, and the formulation is suitable (including safe, in a sustained therapeutically effective amount, and tolerable) for infusion to a human for a period of 24 hours or more. In one aspect, the formulation (reconstituted formulation) has a pH of greater than 9.0, greater than 9.5, greater than 10.0, or greater than 10.5, e.g., 9.3 to 11, whereas the buffering agent has buffering capacity in a pH range of 7 to 9.

In some embodiments, the formulation is able to maintain a stable pH. For example, the formulation has a pH that is within about 0.1 or about 0.2 pH unit after storage at one, two, or four weeks, or 3 months, 6 months, or 12 months at or about 25° C./60% relative humidity (RH), 40° C./75% RH, or 70° C./75% RH. In some embodiments, the glyburide has increased stability as compared to the same formulation that either lacks a buffering agent or has a buffering agent that has a buffering capacity overlapping with the pH of the formulation. In some aspects, the stability can be determined by measuring generation of degradation products. For example, the degradation products can be measured by HPLC. In some aspects, the degradation products are quantified based on relative retention time (RRT) on HPLC.

In some aspects, the buffering agent is a combination of Tris-HCl and Tris-base. In some aspects the weight ratio between Tris-HCl and Tris-base is 7:4, 6.7:4.5, 6.5:4.7, 6.4:4.8, 6.3:4.9, 6.2:5.0, or 6.1:5.1.

In some aspects, a lyophilized glyburide formulation comprises about 5 to 15%, 6 to 14%, 7 to 13%, 8 to 12%, 9 to 13%, or 10 to 12% (w/w) of the buffering agent. In some aspects, a reconstituted glyburide formulation comprises about 5 to 15%, 6 to 14%, 7 to 13%, 8 to 12%, 9 to 13%, or 10 to 12% (w/w) of the buffering agent. In some aspects, a reconstituted glyburide formulation comprises about 1 to 100 mM, 2 to 80 mM, 3 to 70 mM, 4 to 60 mM, 5 to 50 mM, 6 to 40 mM, 7 to 30 mM, 8 to 25 mM, 9 to 23 mM, 10 to 21 mM, 11 mM, 12 mM, 13 mM, 14 mM, 15 mM, 16 mM, 17 mM, 18 mM, 19 mM, or 20 mM of the buffering agent. In some aspects, a reconstituted glyburide formulation comprises about 1 to 5 mg/ml, 1.2 to 4 mg/ml, 1.5 to 3.5 mg/ml, or 2 to 3 mg/ml of the buffering agent.

In some aspects, the buffering agent is a buffer having a pH of 7.8 to 9, 8.1 to 8.9, 8.2 to 8.8, 8.3 to 8.7, 8.4 to 8.6, or 8.5.

In some aspects, the present disclosure includes use of an admixture device that enables reconstitution and transfer of the lyophilized formulation between a vial and an IV bag prior to administration. The admixture device may be a needle-free device. The admixture device may meet the requirements of USP <797>. The admixture device may have a dual channel design providing dedicated fluid pathways into and out of the IV bag. In one aspect, the present disclosure includes use of an admixture device as described in U.S. Pat. No. 8,551,067 (Zinger), which is incorporated herein by reference in its entirety. In one aspect, the present disclosure includes use of an admixture device as described in U.S. Pat. No. 10,688,295 (Lev), which is incorporated herein by reference in its entirety. In some aspects, the present disclosure includes a method of using the VIAL2BAG®, VIAL2BAG ADVANCED™, and/or MIX2VIAL® admixture devices to reconstitute and transfer the lyophilized formulation between a vial and an IV bag prior to administration.

In a second aspect, the base is a strong base having a pKb of 0.1 to 1.5. Any pharmaceutically acceptable strong base may be used. For example, and without limiting the foregoing disclosure, the base may be NaOH, CaOH, or KOH.

In a third aspect, the formulation of the present disclosure includes a specific weight ratio between the glyburide and the base to achieve a pH target in a range of 9.8 to 11.2, 9.9 to 11.1, 10.0 to 11.0, 10.1 to 10.9, 10.2 to 10.8, 10.3 to 10.7, or 10.4 to 10.6, in the formulation.

In some aspects, the formulation of the present disclosure includes a specific molar ratio between the base and the glyburide is 5.0 to 6.7:1, 5.1 to 6.6:1, 5.2 to 6.5:1, 5.3 to 6.4:1, 5.4 to 6.3:1, 5.5 to 6.2:1, 5.6 to 6.1:1, 5.7 to 6.0:1, or 5.2:1, 5.3:1, 5.4:1, 5.5:1, or 5.6:1, in the formulation. The molar ratio used according to the present disclosure is unexpectedly about 2-fold higher than those used in prior art glyburide formulations.

In some aspects, the lyophilized glyburide formulation comprises about 2 to 3.5%, 2.5 to 3.3%, 2.7 to 3.1%, 2.8 to 2.98%, 2.9 to 2.97%, or 2.94 to 2.96% (w/w) of the glyburide.

In some aspects, the lyophilized glyburide formulation comprises about 70 to 93%, 75 to 92%, 80 to 91%, 84 to 90%, 86 to 89%, or 87 to 89% (w/w) of a sugar alcohol of the present disclosure. In some aspects, the sugar alcohol is mannitol, sorbitol, xylitol, or a combination thereof. In some aspects, the sugar alcohol is mannitol.

In some aspects, the formulation of the present disclosure includes a specific weight ratio between the sugar alcohol and the glyburide in the formulation.

In some aspects, the formulation of the present disclosure includes a specific weight ratio between the sugar alcohol and the buffering agent is 5 to 15:1, 6 to 14:1, 7 to 13:1, 8 to 12:1, 9 to 11:1, 9.5:1, 10:1, or 10.5:1 in the formulation.

In some aspects, a reconstituted glyburide formulation comprises about 20 to 40 mg/ml, 24 to 36 mg/ml, 26 to 34 mg/ml, 38 to 32 mg/ml, 29 mg/ml, 30 mg/ml, or 31 mg/ml of the sugar alcohol.

In some aspects, a reconstituted glyburide formulation has a pH of about 9.3 to 11, 9.4 to 10.9, 9.5 to 10.8, 9.6 to 10.7, 9.7 to 10.6, 9.6 to 10.5, 9.7, 9.8, 9.9, 10.0, 10.1, 10.2, 10.3, or 10.4. In some aspects, a reconstituted glyburide formulation has a pH of 9.5 to 10.0.

In some aspects, the glyburide is a free acid or pharmaceutically acceptable salt thereof. In some aspects the glyburide formulation comprises a sodium addition salt of glyburide. As used throughout this disclosure, recitations of "glyburide" may also describe salts, esters, hydrates, solvates, racemates, tautomers, stereoisomers, and/or optically active forms thereof.

In some aspects, the present disclosure includes preparing aqueous solutions of glyburide in a buffer of the present disclosure in the concentrations described herein, adding a base of the present disclosure in the weight ratios to glyburide described herein, and freeze-drying the solution to provide a lyophilized solid composition. In some aspects the aqueous solution may further contain a sugar alcohol of the present disclosure in the concentrations described herein.

In some aspects, formulations of the present disclosure are free of one or more of cyclodextrin(s), meglumine, sugar(s) such as, e.g., fructose, mannose, galactose, arabinose, xylose and ribose, etc., and also oligosaccharides such as disaccharides (maltose, lactose, sucrose, trehalose, etc.) and trisaccharides (e.g. raffinose, maltotriose, etc.), salt(s), alcohol(s) such as, e.g., ethanol, diethanolamine, Britton-Robinson buffer, lactate, acetate, glutamate, glycine, citrate, succinate, surfactants, polysorbate(s), solubilizing polymers, such as polyethylene glycol(s), inorganic or organic acids such as methanesulfonic acid, lactic acid, tartaric acid, citric acid, succinic acid, hydrochloric acid, hydrobromic acid, sulfuric acid, nitric acid, ethanesulfonic acid, p-toluenesulfonic acid, salicylic acid and the like, choline, n-methyl glucamine, diethylamine, procaine and the like.

In some aspects, the reconstituted formulation of the present disclosure has an osmolarity of between about 250 milliOsmoles/liter (mOsm) and about 350 mOsm; or between about 280 mOsm and about 320 mOsm; or between about 290 mOsm and about 310 mOsm.

The present disclosure provides methods and formulations enabling the provision of glyburide formulations having significantly higher glyburide solubility in the dosing solutions, i.e., about 3-fold higher than prior art intravenous glyburide dosing solutions (i.e., greater than 15 μg/ml in contrast to less than 5.7 μg/ml in prior art intravenous glyburide dosing solutions). Further, there is no detectable loss of glyburide due to precipitation or sorption even at these three-fold higher concentrations.

In some aspects, a diluted (also referred to herein as the "final dosing" formulation) glyburide formulation according to the present disclosure has a glyburide concentration of 7.2 (±0.2) μg/mL and infusion pH to ~8.3 (±0.1).

In some aspects, a final dosing glyburide formulation has a pH of 7.8 to 9.0, 7.9 to 9.0, 8.0 to 9.0. In some aspects, a final dosing glyburide formulation has a pH of 7.8 to 9, 7.9, 8.0, 8.1, 8.2, 8.3, 8.4, 8.5, 8.6, 8.7, 8.8, or 8.9.

In some aspects, a final dosing glyburide formulation has a buffer concentration of about 0.1 to 0.5 mM, about 0.15 to 0.4 mM, about 0.2 to 0.3 mM, or about 0.2 mM.

In some aspects, a diluted glyburide formulation of the present disclosure is diluted into 500 mL IV infusion bag, thereby reducing the amount of infusion liquids administered to the subject. In view of the increased solubility, stability, and minimized sorption to medical containers, the formulation of the present disclosure makes it possible to use a more concentrated dosing formulation, thereby delivering a consistent therapeutic dose over the infusion period while using significantly less infusion fluids.

In some aspects, the present disclosure provides a method for decreasing the volume of infusion liquids administered to the subject by about 25-30% over the infusion period, e.g., from about 2 L to 1.5 L for a four day infusion period or from about 1.5 L to 1.1 L for a three day infusion period.

In some aspects, due to the advantages of the present invention, a diluted glyburide formulation can be administered at a slower rate than prior art intravenous glyburide formulations. For example, the infusion rates can be decreased to about 80% the rate of infusion used for infusing prior art intravenous glyburide formulations, e.g., 23 ml/hour for first six hours and 15.9 ml/hour thereafter versus 29 ml/hour for first six hours and 20 ml/hour thereafter compared to prior art intravenous glyburide formulations.

In some aspects, the present disclosure includes sterilizing the formulations of the present disclosure. In some aspects, the formulation may be filter sterilized. In some aspects, the formulation may be sterilized to have zero bioburden. In some aspects, the product of the present disclosure may be terminally sterilized. In some aspects, the product is sterilized with gamma irradiation. In some aspects, the product is sterilized by electron beam, X-ray, hydrogen peroxide, or ethylene oxide. In some aspects, the product may be a powder, a solution, a vial, a kit, a prefilled syringe, an injection device, a cartridge, an on body injector, an auto-injector, an infusion bag, or any other container or container set suitable for storage, infusion and/or injection of the products of the present disclosure. In some aspects, the product satisfies a "sterility assurance level" or "SAL" of $10^{-3}$, $10^{-4}$, or $10^{-6}$.

In some aspects, the present disclosure provides a compound having the following structure:

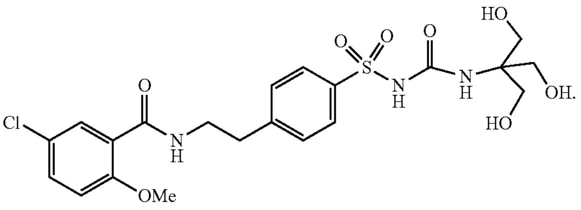 [SMILES: COc1ccc(Cl)cc1C(=O)NCCc1ccc(S(=O)(=O)NC(=O)NC(CO)(CO)CO)cc1]

In some aspects, the present disclosure provides formulations comprising glyburide and a compound having the following structure:

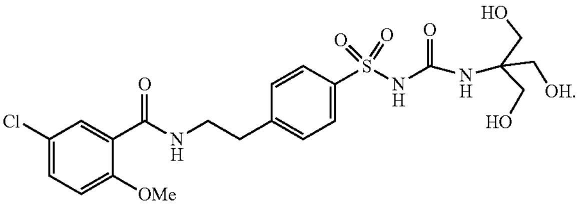 [SMILES: COc1ccc(Cl)cc1C(=O)NCCc1ccc(S(=O)(=O)NC(=O)NC(CO)(CO)CO)cc1]

In some aspects, the present disclosure provides lyophilized formulations containing a compound having the following structure:

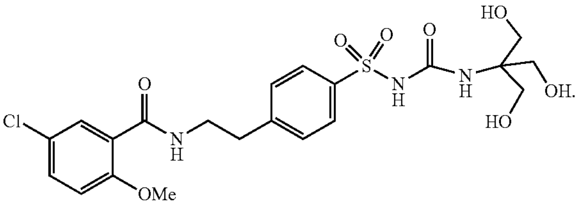 [SMILES: COc1ccc(Cl)cc1C(=O)NCCc1ccc(S(=O)(=O)NC(=O)NC(CO)(CO)CO)cc1]

In some aspects, formulations may contain less than 1 wt. %, less than 0.5 wt. %, less than 0.3 wt. %, less than 0.1 wt. %, less than 0.05 wt. %, e.g., 0.001 to 0.04 wt. %, 0.01 to 0.03 wt. %, 0.01, 0.02, or 0.03 wt. % of the compound.

Kits having features of the invention may include liquid solutions of glyburide, and/or liquid solutions of glyburide together with one or more compounds, and may include instructions for the use of such liquid solutions. For example, instructions for the use of such liquid solutions may include instructions for freeze-drying such solutions in order to obtain a lyophilized formulation of the compound or compounds of interest. Alternatively, or in addition, kits having features of the invention may include lyophilized formulations of glyburide, and/or lyophilized formulations of glyburide together with one or more compounds, and/or lyophilized formulations of glyburide together with one or more liquids for reconstitution, and may include instructions for the use of such lyophilized formulations. For example, instructions for the use of such lyophilized formulations may include instructions for re-constituting such lyophilized formulations to provide solutions, preferably sterile solutions, suitable for use in pharmaceutical application. In some aspects, the vial contains the buffer of the present disclosure at a concentration of 6 to 40 mM, 7 to 30 mM, 8 to 25 mM, 9 to 20 mM, or 10 to 15 mM.

Accordingly, the formulations and kits disclosed herein provide improved medicaments and treatments, and the methods disclosed herein provide improved methods for making medicaments and for treating patients. The present disclosure includes a method of treating a patient suffering from a disorder selected from the group consisting of stroke, neuronal cell swelling, traumatic brain injury, spinal cord injury, organ ischemia, acute coronary syndrome, myocardial infarction, sepsis, and diabetes, comprising administering intravenously to a patient in need thereof an effective amount of an aqueous pharmaceutical composition described herein. In certain instances, the disorder is stroke. In certain instances, the patient is a human. In certain other instances, the disorder is stroke, ischemia, hypoxia/ischemia, spinal cord injury, brain trauma, or other brain injury. A patient in need of treatment may be, for example, a patient suffering from diabetes, or from hemorrhage, or other disorder or condition. A patient in need of treatment may be, for example, a patient suffering from ischemia of any organ, or organs, or system. Such a system may be, for example, the nervous system, including a portion of the nervous system, or the cardiovascular system, or a part of the cardiovascular system. Such an organ may be, for example, the brain, the heart, a muscle, or other organ. A patient in need of treatment may be any patient who may benefit from administration of the formulations, compositions, and/or contents of the kits disclosed herein. Further examples of a patient in need of treatment include patients suffering from a disorder selected from the group consisting of stroke, hemorrhage, neuronal cell swelling, traumatic brain injury, spinal cord injury, organ ischemia, acute coronary syndrome, myocardial infarction, and sepsis.

In some aspects, the formulations, methods, and kits of the present disclosure will be provide tolerable, safe, effective, and predictable infusion dosing to a patient for an extended period of time, e.g., 3, 6, 12, 24, 48, 72, 96, 120 hours or longer.

The present disclosure includes liquid formulations, which include undiluted liquid formulations as well as final dosing solutions for bolus administration.

Liquid formulations disclosed herein may be used for infusion, such as infusion over an extended period of time, into the vasculature, cerebrospinal fluid, or other destination of administration, of a patient suffering from stroke, head trauma, spinal cord injury, cardiac arrest leading to an interruption of blood flow to the brain, or other condition in which the sufferer is at risk of brain swelling or neural cell swelling. In a yet further example, the liquid formulations disclosed herein may be used for intracerebroventricular or intrathecal administration to a patient suffering from stroke, head trauma, spinal cord injury, cardiac arrest leading to an interruption of blood flow to the brain, or other condition in which the sufferer is at risk of brain swelling or neural cell swelling. Administration of glyburide via liquid formulation, and in particular via intra-arterial or intravenous administration, provides rapid and readily controlled increase in circulating glyburide concentrations, providing rapid onset of treatment which allows rapid adjustment and ready maintenance of circulating glyburide concentrations.

The inventors encountered numerous confounding challenges in developing an intravenous glyburide formulation, particularly for use in emergency medical settings. Glyburide is practically insoluble in water at physiological pH, has low stability in that it precipitates, and adsorbs to plastic medical containers, tubing, and filters, particularly at low and physiological pHs. Further, the inventors discovered a degradation product that was formed. Particularly at relatively low ratios of base to glyburide, the percentage of degradation product formed increases. While higher pHs are used to solubilize glyburide, it is not possible to intravenously administer formulations having such high pHs. Further, due to the low solubility and unpredictable sorption to medical plastic materials, the inventors encountered problems including, but not limited to: 1) inability to quickly and predictably administer a therapeutic dose; 2) wastage of drug product that was adsorbed to the materials rather than injected into the patient; and 3) the need to administer large amounts of saline infusion solution to patients.

As shown in FIG. 1, in a mock infusion test with various administration materials using prior art glyburide formulations, there is significant sorption immediately at the start of infusion, and the concentration changes, but does not recover throughout the entirety of the infusion period. Moreover, the change in concentration of glyburide is different depending on material of the administration set. Thus, there was significant unpredictability in how much of the drug product would be administered to a given patient at any given time depending on various factors.

Figure 2:
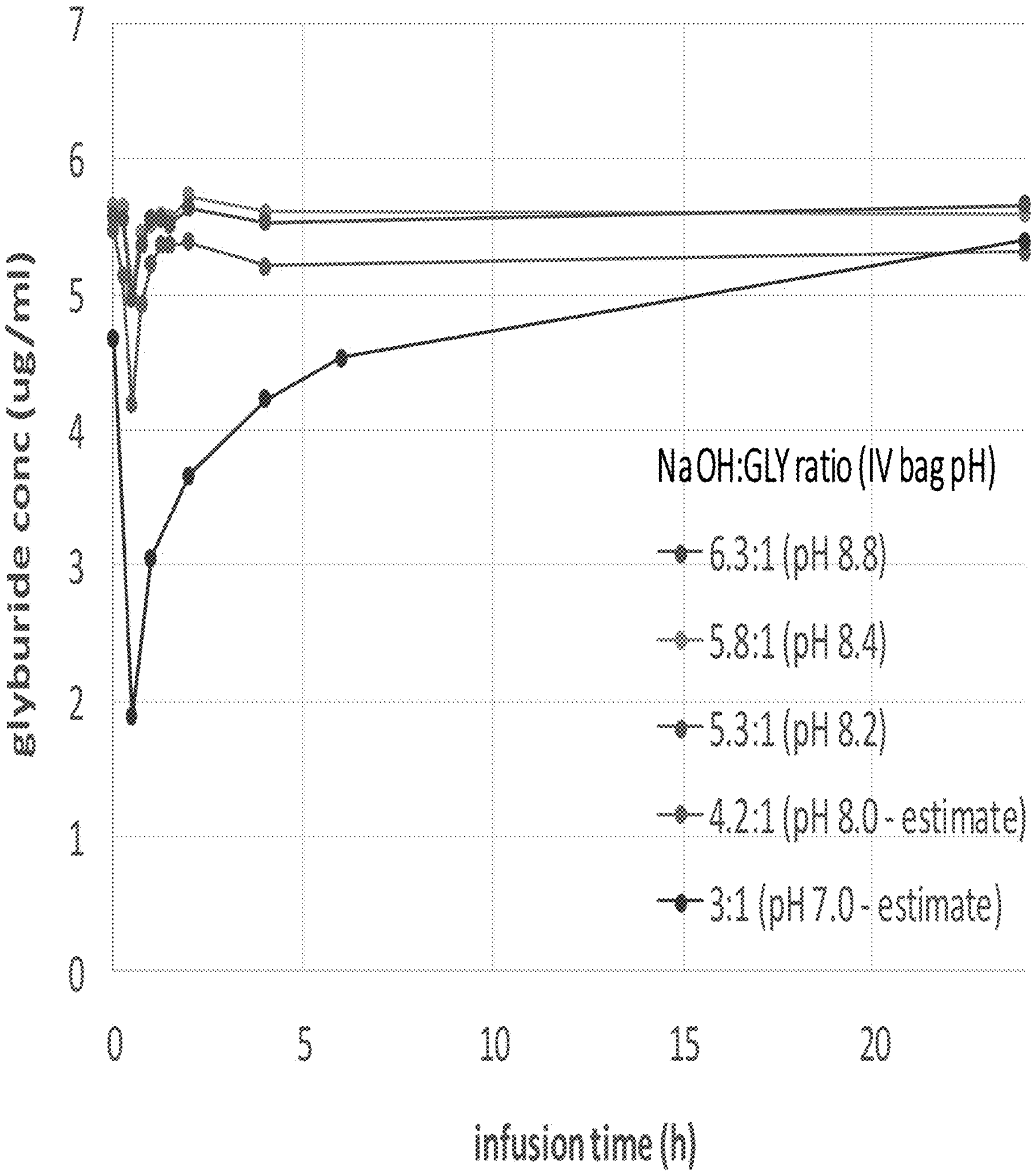
FIG. 2 shows the effects of different base to glyburide ratios on the sorption of prior art glyburide intravenous formulations to PVC administration sets.

Further, as shown in FIG. 2, the present inventors tested glyburide formulations containing the prior art components, but varied the ratio of NaOH to glyburide to determine the effects of the ratios on sorption. The inventors found that, there was significant sorption immediately at the start of infusion and the rate of recovery of the glyburide concentration over the course of the infusion period varied significantly between formulations having various ratios of base to glyburide. There was an at least 10% initial drop in the glyburide concentration and the drop was as high as about 40% when the NaOH:GLY ratio was 3:1. Specifically, prior art formulations of glyburide with varying NaOH:GLY molar ratios were reconstituted and diluted into a 1 L saline bag. A mock IV infusion was set up using PVC administration sets and the glyburide concentration of the infusate at the indicated time points was measured (and expressed as the percentage of the initial concentration of glyburide in the IV bag). At lower NaOH:GLY ratios, a longer period of time is required for the drug concentration to recover. However, it was impossible to use higher base to glyburide ratios in the prior art glyburide formulations in order to avoid the sorption problem because using sufficiently high base to glyburide ratios resulted in reconstituted formulations that had pHs too high for infusion into human patients, i.e., having a pH of ~10, whereas the maximum pH that is considered acceptable for human infusion by the industry is pH 9 according to the 2016 Infusion Therapy Standards of Practice.

As such, the present disclosure provides formulations, including lyophilized, reconstituted, and diluted (final dosing) formulations that solve the aforementioned confounding problems including sorption to medical containers, extremely low solubility, low stability, high wastage, and need to infuse large amounts of saline to deliver the drug.

It was found through experiments that it was necessary to use specific combinations of specific buffering agents of the present disclosure, base, glyburide, and a sugar alcohol, in specific ranges of amounts, and in specific ratios to each other in making the formulations that could provide sufficient solubility, stability, therapeutic effect, safety for infusion to humans, while avoiding sorption to medical containers, formation of degradation products, and need to administer large volumes of saline infusion solution to deliver the therapeutic doses. It was unexpectedly found to be necessary to use a buffering agent having a buffering capacity outside of the pH of the glyburide formulation.

Figure 3:
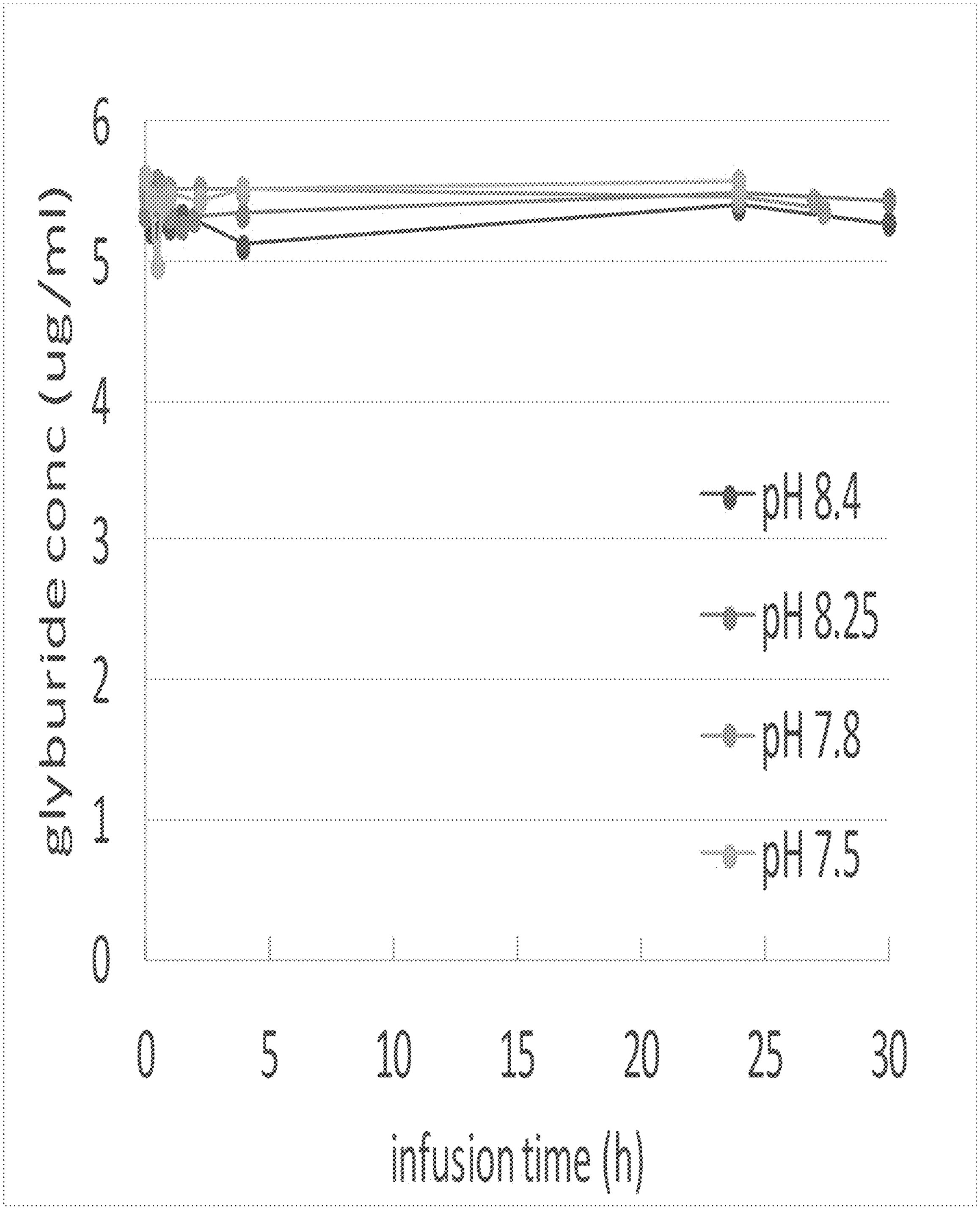
FIG. 3 shows the effect of pH of final dosing formulation in formulations of the present disclosure in terms of sorption to PVC administration sets.
Figure 6:
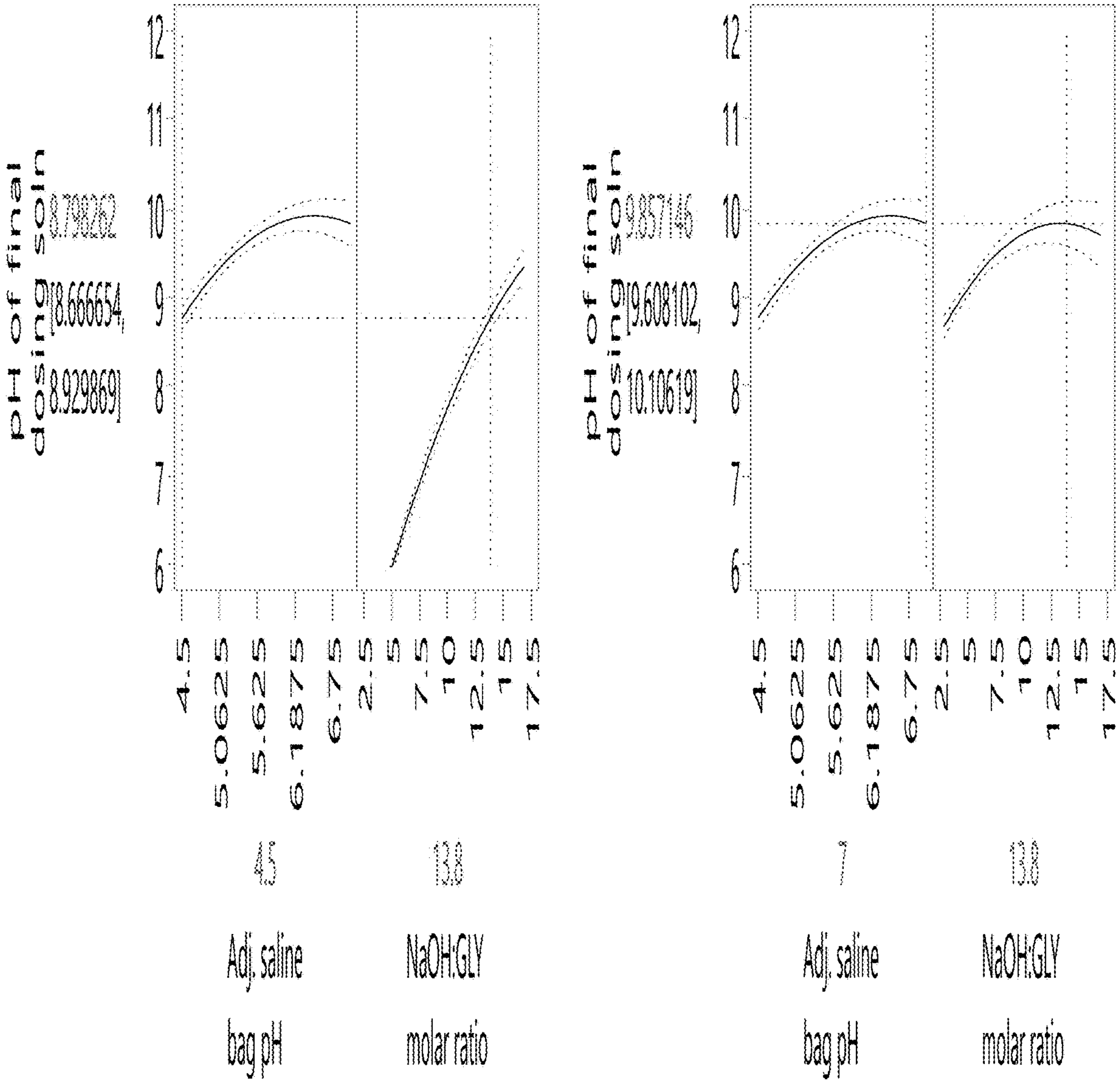
FIG. 6 shows NaOH:GLY molar ratio necessary to use in prior art glyburide formulations in order to eliminate sorption to PVC administration sets. (Left) With an initial saline pH of 4.5, a NaOH:GLY molar ratio of 13.8 is required in the clinical formulation to achieve a pH of 8.8 in the final dosing solution. (Right) If drug product with a NaOH:GLY molar ratio of 13.8 is reconstituted into saline with a pH of 7, the resulting pH in the final dosing solution would be 9.9, which is outside the pH range of typical infusion solutions (even considering the pH drop in a non-buffered system during infusion).

In order to avoid the initial dip in glyburide concentration caused by sorption to the administration sets, a pH-escalating experiment using formulations according to the present disclosure were conducted. As shown in FIG. 3, it was found that if the pH of the diluted (final dosing) formulations according to the present disclosure were less than 7.8, then there was an at least 10% dip in glyburide concentration. Thus, it was recognized that by producing the glyburide formulation of the present disclosure that consistently maintains a pH of at least 7.8, and that has a pH of 9.0 or less when diluted into the infusion solution, e.g., saline solution, it is possible to eliminate sorption to PVC administration sets. As shown in FIG. 6, (left), with an initial saline pH of 4.5, a NaOH:GLY molar ratio of 13.8 was required in the prior art glyburide formulation to achieve a pH of 8.8 in the final dosing solution. (Right) If drug product with a NaOH:GLY molar ratio of 13.8 is reconstituted into saline with a pH of 7, the resulting pH in the final dosing solution would be 9.9, which is outside the pH range of acceptable infusion solutions.

Figure 4:
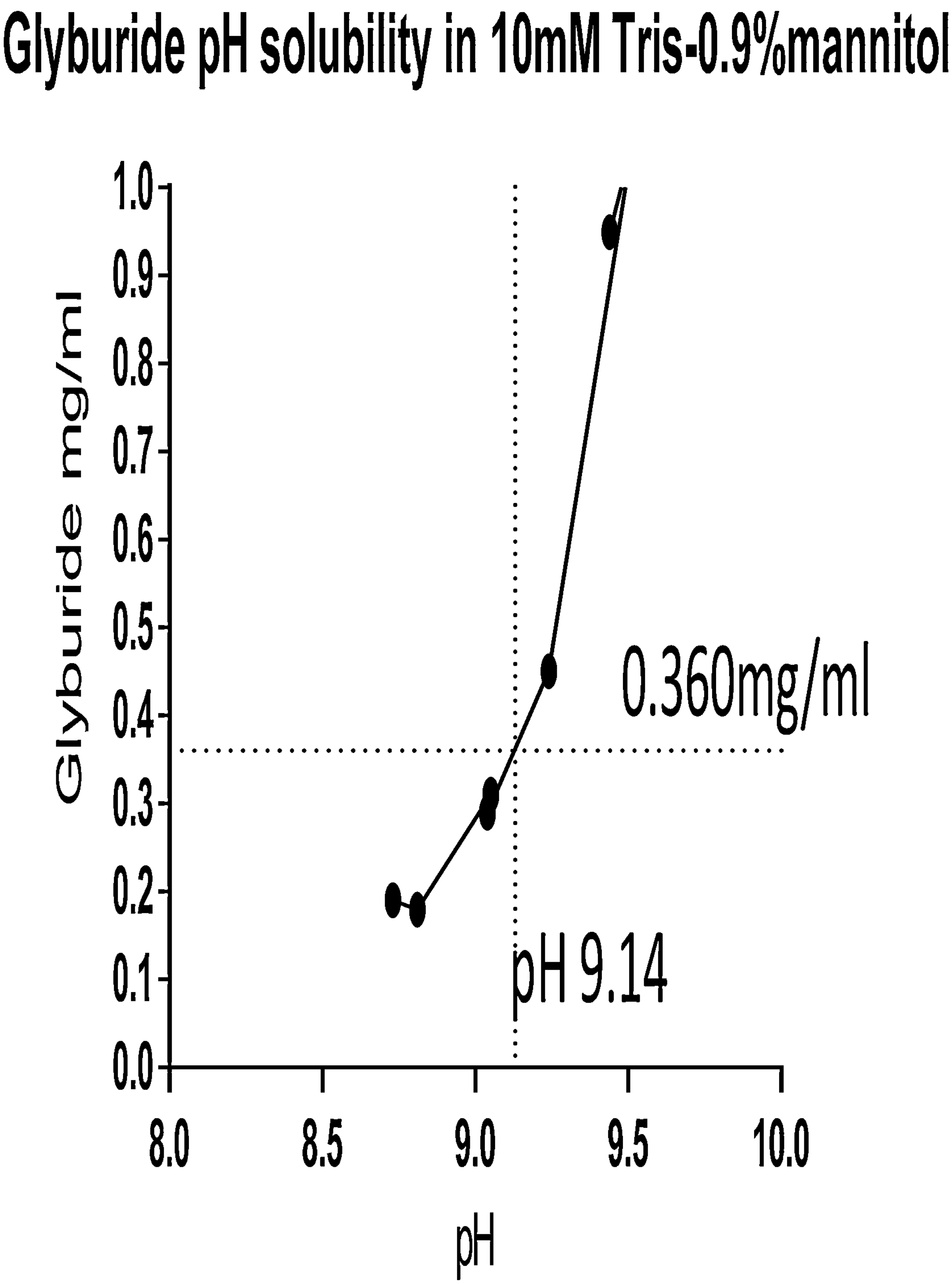
FIG. 4 shows the glyburide solubility of formulations of the present disclosure in a 10 mM Tris/0.9% mannitol solution to simulate the buffer system after drug product reconstitution.
Figure 5:
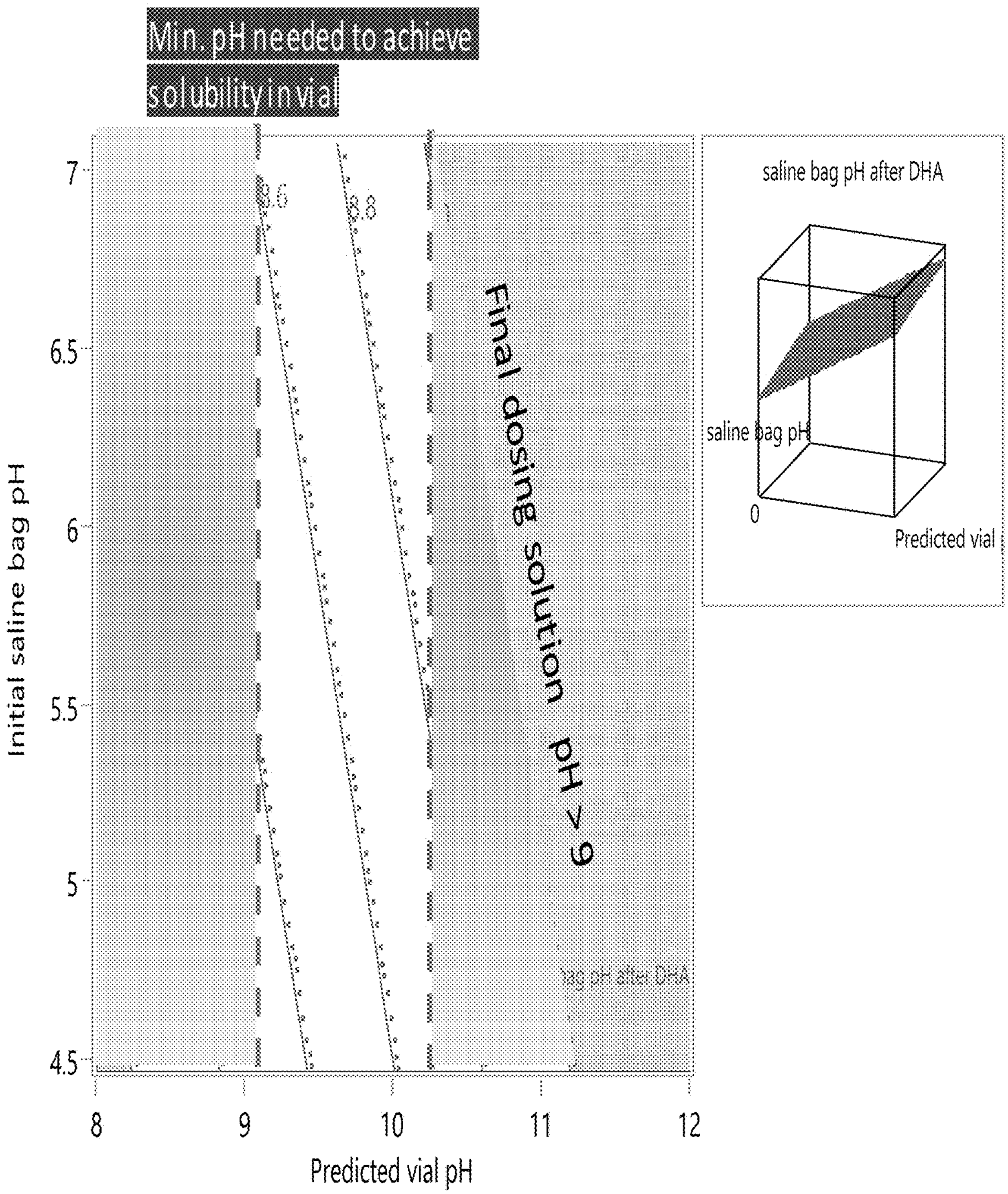
FIG. 5 shows the relationship between vial pH after reconstitution of formulations of the present disclosure, the initial saline pH, and the pH of the final dosing solution (contour lines).

An additional critical requirement was that, after reconstitution, the reconstituted formulation must remain sufficiently stable and soluble. As an example, in an experiment using 10 mM Tris and 0.9% mannitol, as shown in FIG. 4, it was determined that for a drug product vial containing 6 mg glyburide and reconstitution volume of 20 ml, the resulting concentration is 0.3 mg/ml glyburide. Assuming a 20% buffer in concentration (0.360 mg/ml), a minimum vial pH of 9.14 was required to ensure solution stability after reconstitution. Using Tris concentrations lower than 10 mM also were sufficient to protect against instability, sorption, and low solubility, e.g., reconstituting a 6 mg/vial drug product with 20 ml of a 5 mM solution, and further dilution into 1 L saline bag; buffer concentration in final dosing solution ~0.1 mM Tris, was sufficient. Based on these data, the necessary parameters for minimum reconstituted glyburide formulation pH vs. initial saline infusion solution pH were determined as shown in FIG. 5.

The present inventors unexpectedly found that buffering agents having a pKa of 7.7 to 9.2 would provide critical properties for making formulations having the balance of numerous factors so as to be more soluble, more stable, avoid sorption to medical plastics, and have appropriate pH when diluted with infusion solutions to be administrable by infusion to humans. It was unexpected that such buffers would function in the claimed formulations because within the pH range buffered by such agents, glyburide is practically insoluble.

Figure 7:
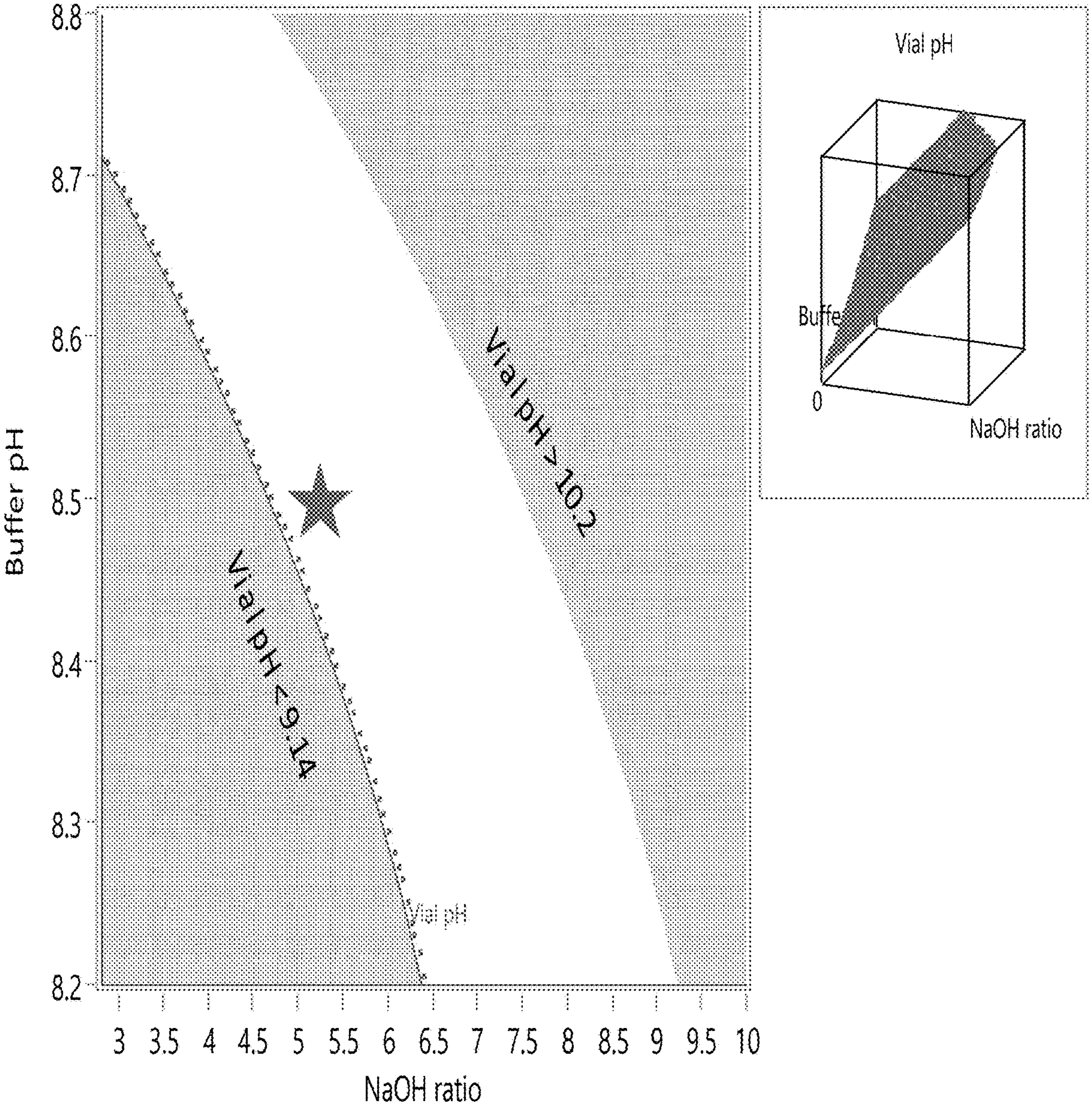
FIG. 7 shows the correlation between NaOH:GLY molar ratio in the drug product, Tris buffer pH (10 mM), and the vial pH after reconstitution (20 ml) in formulations of the present disclosure.

Further, it was necessary to determine the molar ratio of base to glyburide in order to remain sufficiently stable, soluble and avoid sorption to medical plastic materials. While, as shown in FIG. 6, it would have been necessary when using the prior art glyburide formulation to use a NaOH:GLY molar ratio of 13.8 to maintain sufficient stability, solubility, and to avoid sorption, which ratio was too high for use because it resulted in a diluted (final dosing) formulation that was unsafe for infusion into humans (pH of about 10), the formulations of the present disclosure were found to require a much lower ratio of base to glyburide to provide sufficient stability, solubility, and to avoid sorption, and to be safe for infusion into humans when diluted into an infusion solution (final dosing pH of between 7.8 and 9.0). As shown in FIG. 7, the base content in the drug product vial (e.g., 6 mg glyburide/vial) and the pH of the buffer (of the present disclosure) used for reconstitution can be correlated based on the findings of the inventors to produce a formulation having sufficient stability, solubility, and lack of sorption. For example, within the target design space of vial pH (9.1-10.2), the critical NaOH:GLY molar ratio region in the vial and buffer pH was determined. For example, in FIG. 7, when using NaOH as the base, and a buffer at pH 8.5, it is determined that a NaOH:GLY molar ratio of 5.3 should be used (as denoted by the star).

The invention of the present disclosure will be more readily understood by reference to the following examples, which are included merely for purposes of illustration of certain aspects and embodiments of the present invention, and are not intended to limit the scope of disclosed invention.

Example 1

Figure 8:
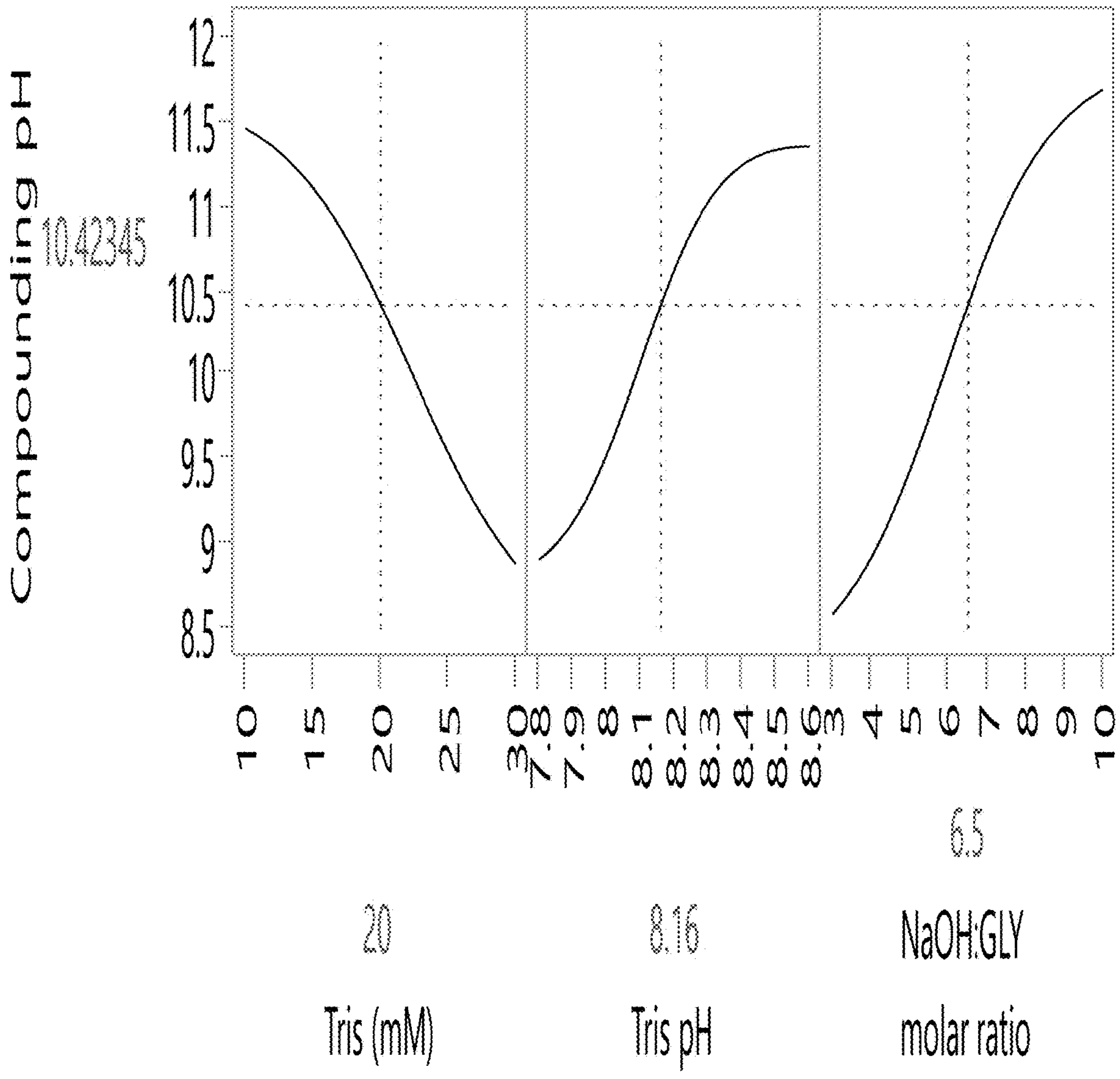
FIG. 8 shows the correlation between Tris concentration, Tris pH, and NaOH content in the formulation on compounding pH (DOE #1-3) based on a non-linear neural network model (Training data set: $R^2$=0.96; Validation data set: $R^2$=0.98).

The solubility and stability of glyburide were tested in formulations having a pH outside of the buffering capacity of Tris buffer. The pKa value of Tris is 8.08 at 25° C. and it has buffering capacity in a pH range of 7.0 to 9.0. In compounding experiments, it was found that a minimum compounding pH of 9.1 was required to maintain bulk solution stability at 1 mg/ml for at least 24 h at room temperature (RT). For formulations with compounding pH <8.9, a cloudy solution was observed, indicating precipitation of glyburide. For formulation compounding pH >9, the compounding pH changes rapidly depending on the buffer and the based to Glyburide molar ratio. For example, as shown in FIG. 8, rapid changes in compound pH depending on Tris pH and NaOH:GLY molar ratio were observed as illustrated by the steep slopes for both these components. This is because Tris buffers effectively in the range of pH 7-9 (i.e. ±1 pH unit from pKa of 8.1). Outside of this pH range, the bulk solution is no longer buffered even with the addition of Tris. To maintain bulk solution stability, it is necessary to increase the compounding pH above 9, which is outside of the buffering range of Tris.

Example 2

Figure 9:
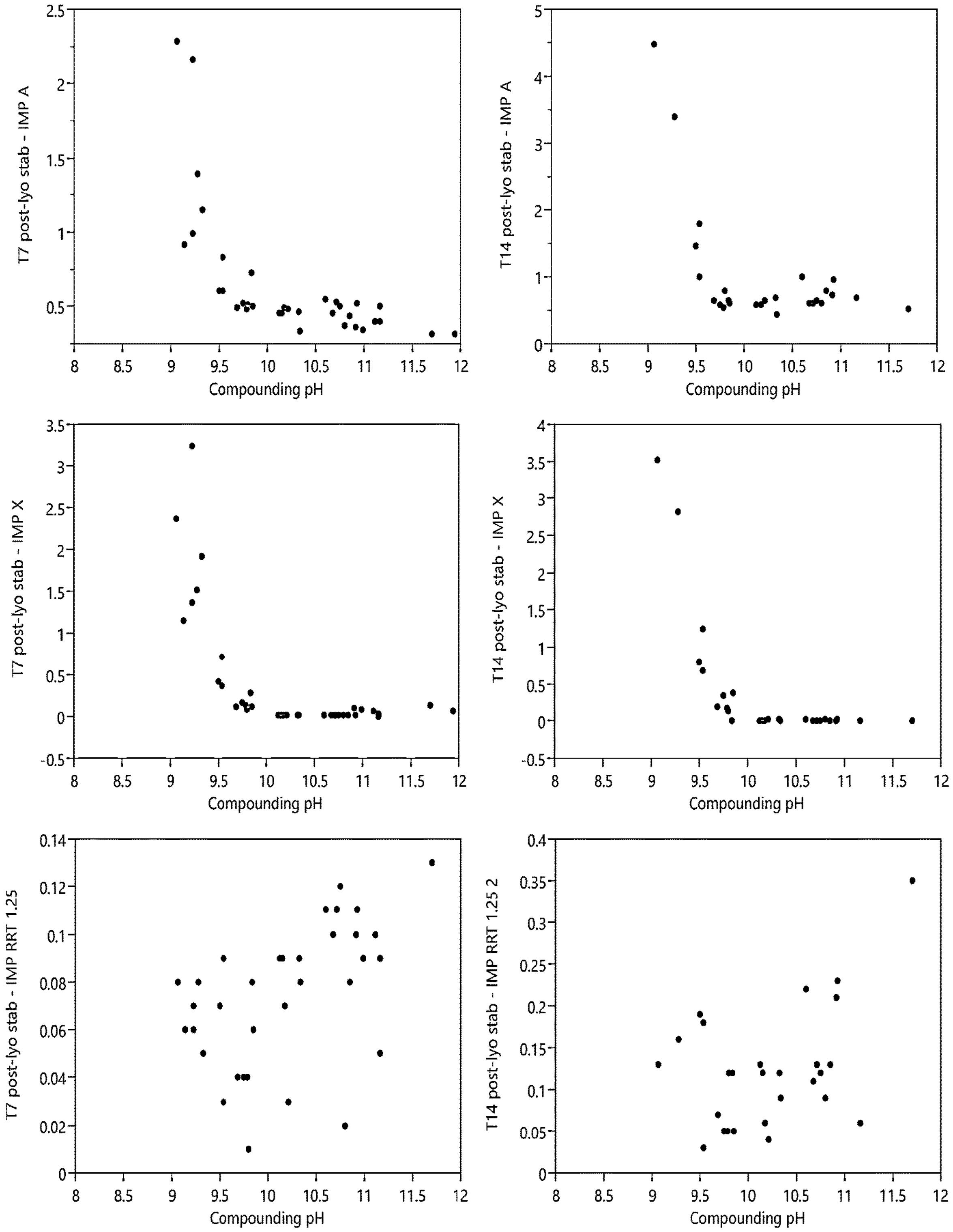
FIG. 9 shows the effect of compounding pH on drug product stability at accelerated conditions (70° C./75 RH) at 7 (left) and 14 days (right). Formulations with varying compounding pH were tested. Formulations were filled into vials (6 ml/vial) and lyophilized. The stability of the DP was assessed for 3 main impurities: (top) Impurity A, (middle), Impurity X, and (bottom) Impurity RRT 1.25.

Solutions having a range of pHs were filled into vials (6 ml/vial) and lyophilized. Stability studies at accelerated conditions (70° C./75 RH) at 7 and 14 days were used to assess the effect of formulation parameters on formation of impurities. A clear dependence on impurity formation on compounding pH was observed for Impurity A and Impurity X as shown in FIG. 9. The generation of both impurities decreased with increasing compounding pH. For Impurity A, above a compounding pH of 9.8, levels were ≤0.5% at 7 d and were ≤1.0% at 14 d. For Impurity X, above a compounding pH of 9.8 levels were ≤0.5% at both 7 and 14 d. Above a compounding pH of 10.3, Impurity X levels were essentially 0%. For Impurity with RRT 1.25, overall levels were low at both 7 and 14 d (<0.2%). As the compounding pH increased, the Impurity with RRT 1.25 showed a weak positive correlation. Based on the accelerated stability studies, a minimum compounding pH of 9.8 will limit the formation of impurities A and X. Overall levels of Impurity with RRT 1.25 were low at all tested pHs.

Figure 10A:
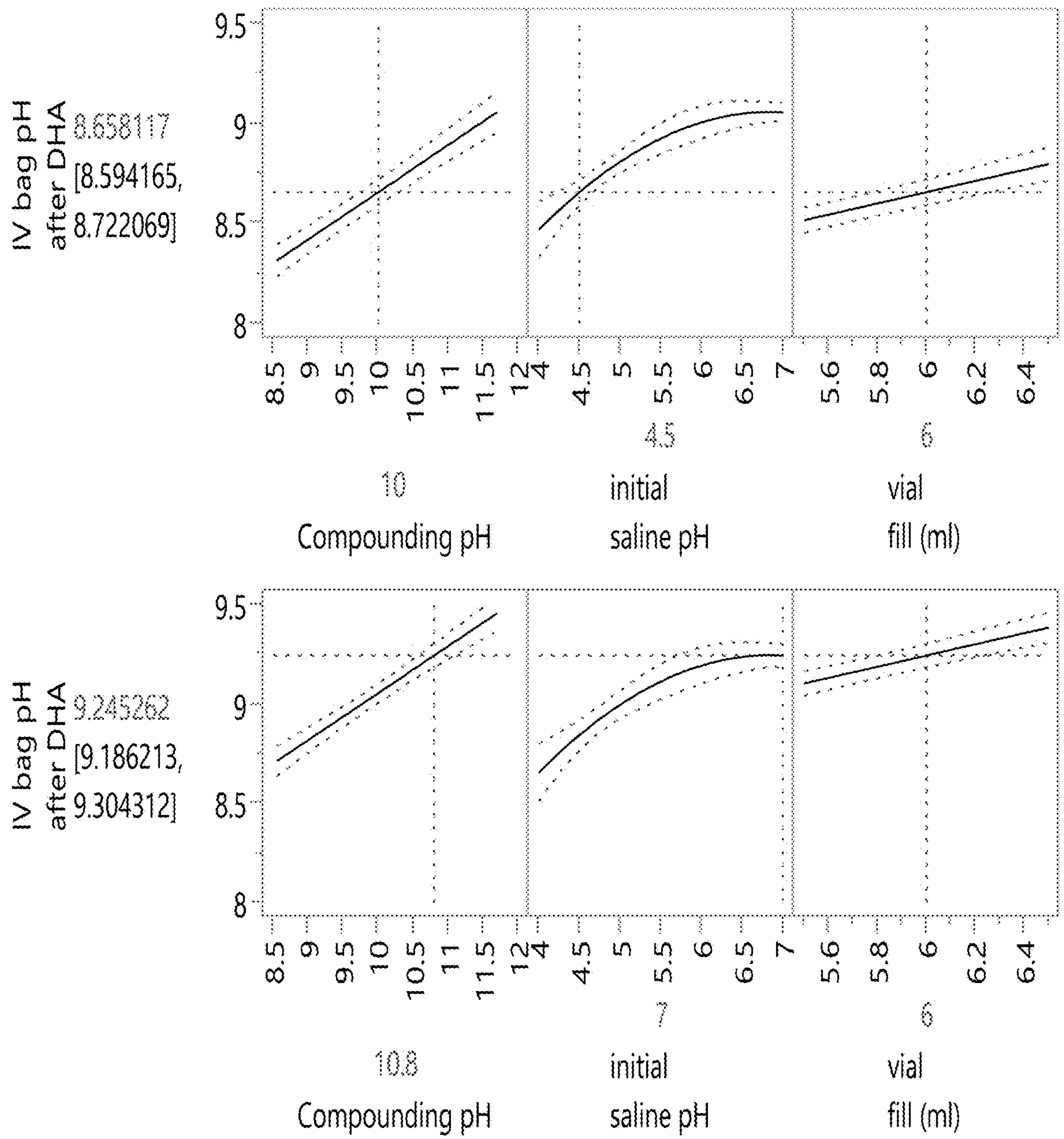
FIGS. 10A and 10B show the effect of compounding pH, initial saline pH, and vial fill on the pH of the final dosing solution based on a linear regression model (Actual by predicted plot: $R^2$=0.91).
Figure 10B:
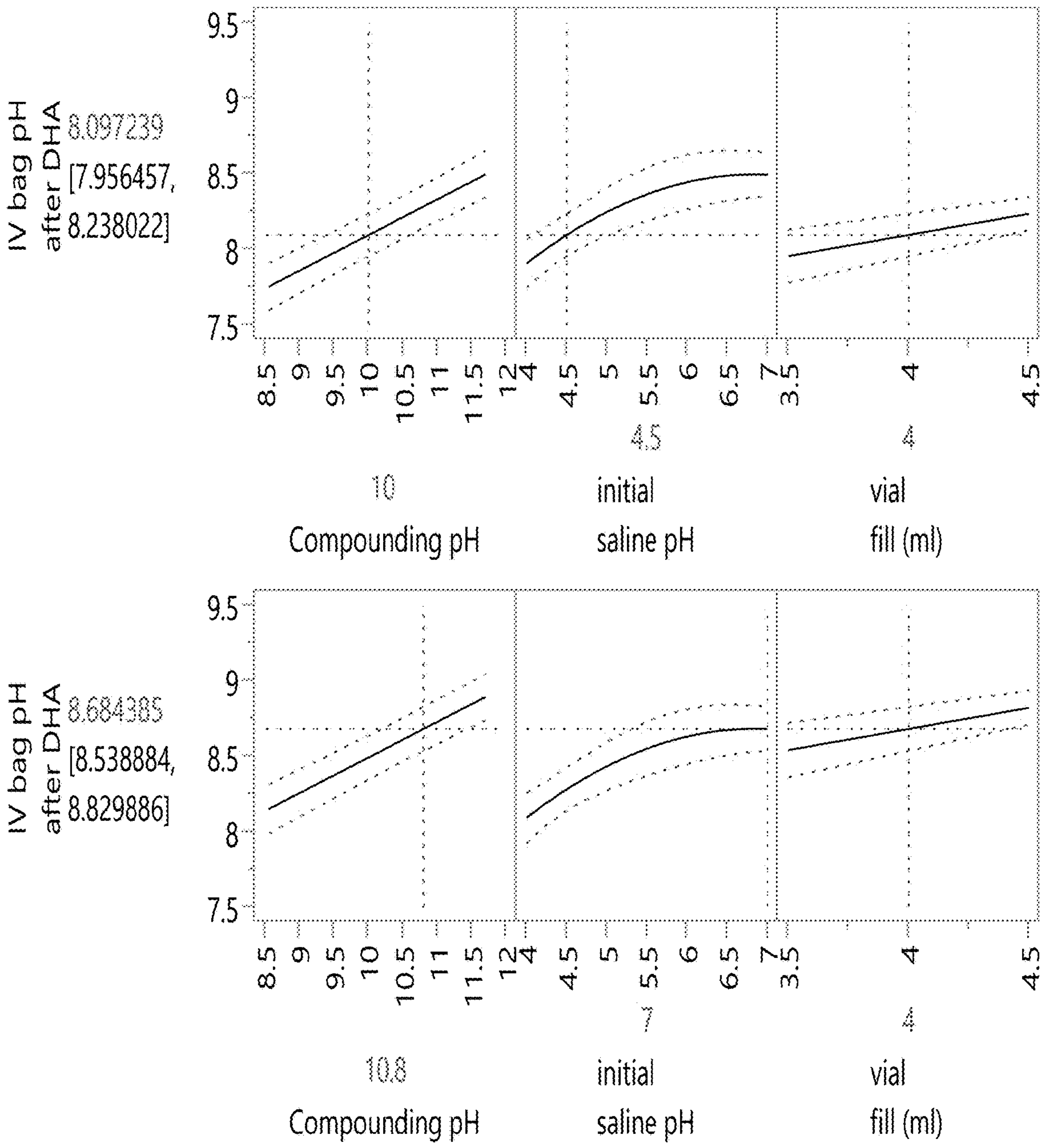

A maximum final dosing pH of 9.2 (after infusion, there is a slight drop in pH to ~9, which is the maximum pH of a solution that can be safely infused to a patient) was used as an upper limit constraint on the compounding pH. Drug reconstitution and dilution experiments were carried out. Experiments were carried out using glyburide with a vial fill volume of 6 ml (i.e. 6 mg of glyburide). Vials were reconstituted with 20 ml water for injection (WFI) and transferred to 500 ml saline bags (instead of the typical 1 L saline bags in order to ensure that the formulation of the present disclosure could be safely administered with less saline than used with prior art glyburide formulations) with an initial pH of either 4.5 or 7 (adjusted with HCl or NaOH). The correlation between compounding pH, initial saline pH, and vial fill with the pH of the final dosing solution is shown in FIG. 10. For a low compounding pH specification of 10.0 (based on accelerated stability studies to limit impurity formation) and initial starting saline pH of 4.5, the expected pH of the final dosing solution is ~8.7 (based on 6 ml vial fill). A maximum compounding pH of 10.8 results in a pH of 9.2 for the final dosing solution (based on a 6 ml vial fill), which represents the highest pH of a solution that can be safely infused into patients. Such formulations avoid sorption of significant amounts of glyburide to PVC administration components as demonstrated below.

The pH of the final dosing solution is also dependent on the drug product vial fill (FIG. 10, right). A formulation having a reduced vial fill of 4 ml (of a 1 mg/ml solution) was produced to as to reduce the glyburide wastage after each day of dosing as shown in the following Table.

| | Exemplary Formulation of the Present Disclosure | Prior art Formulation |
|---|---|---|
| Glyburide/vial (mg) | 4 | 6 |
| Amount of glyburide available after DHA prep (mg) | 3.8 | 5.2 |
| Saline bag volume (ml) | 540 | 1058 |
| Saline withdrawal from bag | 0 | 146 |
| Saline bag concentration (ug/ml) | 6.92 | 5.67 |
| Vol used for admin set flush (ml) | 50.0 | 70 |
| Usable volume per bag | 499.5 | 847.2 |
| 1st bag vol used (ml) | 451.2 | 847.2 |
| 2nd bag vol used (ml) | 386.1 | 376.3 |
| 3rd bag vol used (ml) | 386.1 | 376.3 |
| Residual bag 1 (ml) | 48.3 | 550.3 |
| Residual bag 2 (ml) | 113.4 | 470.9 |
| Residual bag 3 (ml) | 113.4 | 470.9 |
| bag 1 wastage (%) | 10 | 35 |
| bag 2 wastage (%) | 23 | 44 |
| bag 3 wastage (%) | 23 | 44 |

Example 3

Additional reconstitution and dilution studies with drug product with a 4 ml fill were conducted to assess the effect on compounding pH on the pH of the final dosing solution. Within the target compounding pH range of 10-10.8 and using saline throughout the possible pH range or 4.5-7, the pH of the final dosing ranged from 8.1-8.7. It was possible to make a final dosing formulation that was soluble, stable, avoided sorption to PVC/PUR administration components, and was at a pH suitable for infusion to humans.

Through experimentation, it was found that the buffering agent should have a pKa of 7.7 to 9.2, 7.8 to 9.1, 7.9 to 9.0, 8.0 to 8.9, 8.05 to 8.8, 8.1 to 8.7, or any specific pKa in the specified ranges. For example, and without limiting the foregoing disclosure, the buffering agent may be Tris, lysine, arginine, an ethylenediamine, an imidazole, a 4-(2-Hydroxyethyl)morpholine, a triethanolamine, a glucamine, a deanol (dimethylaminoethanol), phosphate, phosphate buffered saline (PBS), or a combination thereof. In studies carried out with buffering agents such as phosphate (pKa 7.21) and glycine (pKa 9.8), it was found that these buffering agents did not effectively stabilize glyburide and did not prevent sorption to medical materials. Specifically, lyophilized glyburide samples containing various amounts of NaOH were reconstituted in 20 ml of sodium phosphate buffer (10 mM, pH 8.0), the pHs were measured and then the reconstituted formulations were diluted in saline infusion solution.

Accordingly, based on these studies, the present disclosure includes the following formulations:

Formulation A (reconstituted, undiluted): 1 mg/ml glyburide, 10, 15, 20, 25, 30, 35, or 40 mg/ml mannitol, 1N NaOH up to a formulation pH of 10.4±0.4, 1.20 mg/ml Tris-base, 1.59 mg/ml Tris-HCl (total 20 mM Tris), and water.

Formulation B (reconstituted, undiluted): 1 mg/ml glyburide, 10, 15, 20, 25, 30, 35, or 40 mg/ml mannitol, 1N NaOH up to a formulation pH of 10.4±0.6, 2.5 to 5 mg/ml arginine, and water.

Formulation C (reconstituted, undiluted): 1 mg/ml glyburide, 10, 15, 20, 25, 30, 35, or 40 mg/ml mannitol, 1N NaOH up to a formulation pH of 10.4±0.6, 2.5 to 5 mg/ml lysine, and water.

Formulation D (reconstituted, undiluted): 1 mg/ml glyburide, 10, 15, 20, 25, 30, 35, or 40 mg/ml mannitol, 1N KOH or CaOH up to a formulation pH of 10.4±0.6, 1.20 mg/ml Tris-base, 1.59 mg/ml Tris-HCl, and water.

Formulation E (reconstituted, undiluted): 1 mg/ml glyburide, 10, 15, 20, 25, 30, 35, or 40 mg/ml mannitol, 1N KOH or CaOH up to a formulation pH of 10.4±0.6, 2.5 to 5 mg/ml arginine, and water.

Formulation F (reconstituted, undiluted): 1 mg/ml glyburide, 10, 15, 20, 25, 30, 35, or 40 mg/ml mannitol, 1N KOH or CaOH up to a formulation pH of 10.4±0.6, 2.5 to 5 mg/ml lysine, and water.

Formulation G (reconstituted, diluted): 7.2 μg/ml glyburide, 0.216 mg/ml mannitol, diluted formulation pH of 8.3±0.1, 0.2 mM Tris, water, and 500 mL saline for infusion.

Example 4

Stability studies were performed on Formulation A having 30 mg/ml mannitol at pHs 9.8, 10.3, and 10.8 at 25° C./60% RH and 40° C./75% RH for up to 6 months as shown in the following tables:

| Sample Description | LYD CAKE STABILITY-25° C./60% RH | | | | | | | | | | | | | | |
|---|---|---|---|---|---|---|---|---|---|---|---|---|---|---|---|
| | Impurity A | | | | | BIO-2005713 (Impurity X) | | | | | RRT 1.23 | | | | |
| | T0 | T1M | T2M | T3M | T6M | T0 | T1M | T2M | T3M | T6M | T0 | 1M | 2M | 3M | 6M |
| DOE7_Form1_pH9.8_20 mM Tris | 0.16 | 0.16 | | 0.16 | 0.16 | 0 | 0 | | 0 | 0 | 0 | 0 | | 0 | 0.01 |
| DOE7_Form2_pH10.3_20 mM Tris | 0.16 | 0.16 | | 0.17 | 0.17 | 0 | 0 | | 0 | 0 | 0 | 0 | | 0.01 | 0.01 |
| DOE7_Form1_pH10.8_20 mM Tris | 0.16 | 0.16 | | 0.16 | 0.16 | 0 | 0 | | 0 | 0 | 0 | 0 | | 0.01 | 0.01 |

| Sample Description | LYD CAKE STABILITY-25° C./60% RH | | | | | | | | | | | | | | | | | |
|---|---|---|---|---|---|---|---|---|---|---|---|---|---|---|---|---|---|---|
| | Impurity A | | | | | | BIO-2005713 (Impurity X) | | | | | | RRT 1.25 | | | | | |
| | T0 | T0.5M | T1M | T2M | T3M | T6M | T0 | T0.5M | T1M | T2M | T3M | T6M | T0 | 0.5M | 1M | 2M | 3M | 6M |
| DOE7_Form1_ pH9.8_20 mM Tris | 0.16 | 0.17 | 0.17 | 0.17 | 0.2 | 0.24 | 0 | 0 | 0 | 0.01 | 0 | 0 | 0 | 0.01 | 0.01 | 0.03 | 0.03 | 0.05 |
| DOE7_Form2_ pH10.3_20 mM Tris | 0.16 | 0.17 | 0.18 | 0.17 | 0.19 | 0.22 | 0 | 0.01 | 0 | 0.03 | 0 | 0 | 0 | 0.01 | 0.02 | 0.03 | 0.03 | 0.06 |
| DOE7_Form1_ pH10.8_20 mM Tris | 0.16 | 0.17 | 0.17 | 0.17 | 0.18 | 0.21 | 0 | 0 | 0 | 0.01 | 0 | 0 | 0 | 0.01 | 0.01 | 0.03 | 0.04 | 0.06 |

It was found that Impurity A levels were below proposed release specifications of either 0.5 or 1%; Impurity X and Impurity RRT 1.25 below the identification thresholds of 0.5%.

The compounding procedure was performed across a temperature range of 15-25° C. it was found that the compounding could be successfully performed across the temperature range. At 15° C., it was found that a NaOH:GLY molar ratio of 5.78-6.4 was suitable. At 21.4° C., it was found that a NaOH:GLY molar ratio of 5.9-6.6 was suitable. At 25° C., it was found that a NaOH:GLY molar ratio of 6.11-6.63 was suitable.

Example 5

Figure 11:
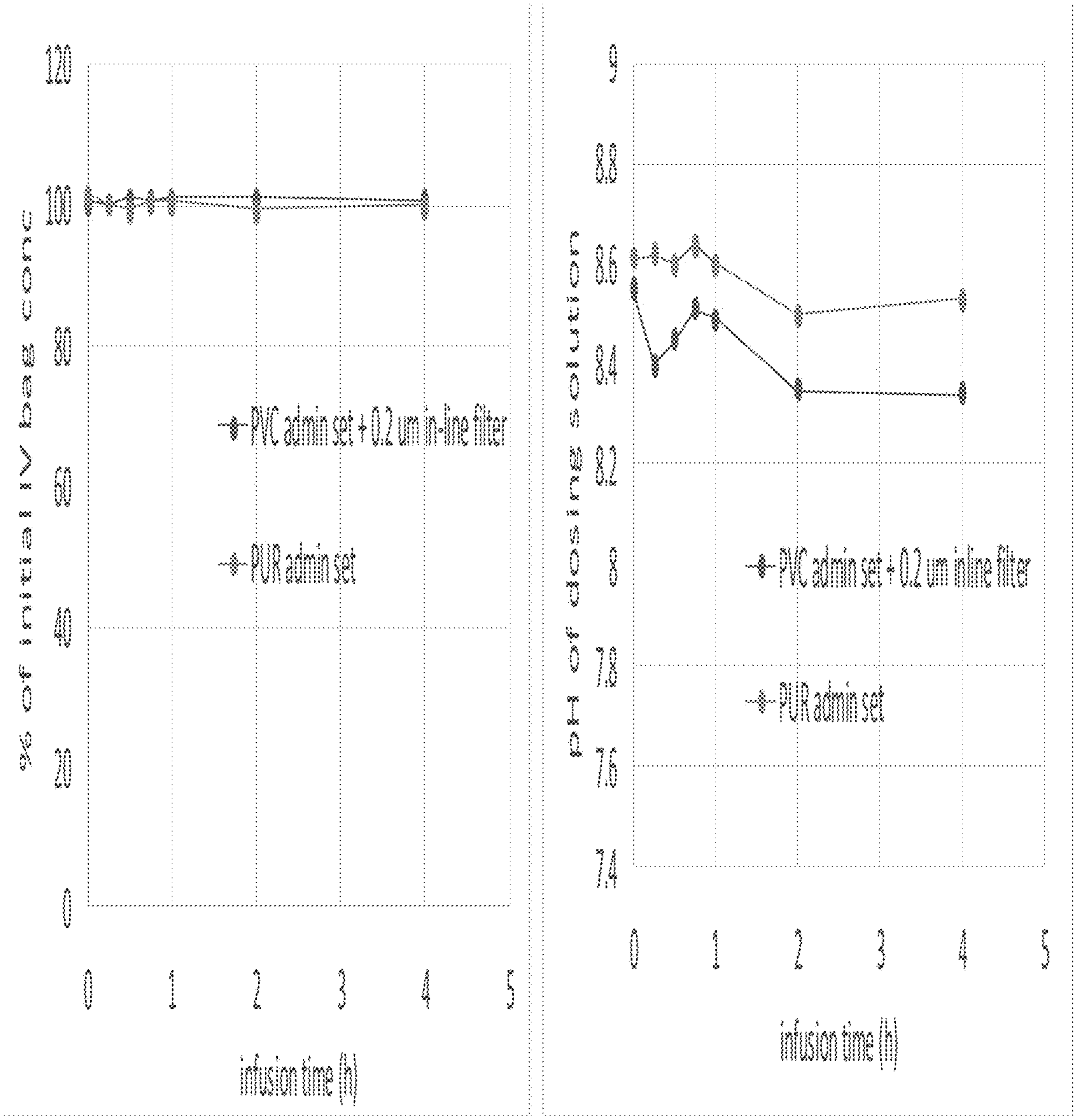
FIG. 11 show mock infusion experiments with the formulation of the present disclsure and PVC/PUR administration sets. (Left) The concentration of glyburide was monitored with two different administration sets as indicated. (Right) The pH of the dosing solution from the distal end of the administration sets was measured at the indicated time points.

To confirm elimination of sorption to administration sets, a mock infusion was performed using the glyburide formulation of the present disclosure (target compounding pH of 9.8). After reconstitution and dilution into an IV bag, the infusion was performed over 4 h (FIG. 11) with a PVC administration set with an in-line 0.2 μm filter and a PUR administration set. As shown in FIG. 11, (left graph) the concentration of glyburide was monitored with two different administration sets as indicated, and (right graph) the pH of the dosing solution from the distal end of the administration sets was measured at the indicated time points. No sorption was observed over the infusion period. The pH of the dosing solution was also tracked at the distal end of administration sets. For PUR administration sets, the pH was maintained at 8.6 for the entirety of the study. For PVC administration sets, the pH dropped from about 8.6 to 8.3. This confirms that incorporation of a buffer of the present disclosure in the final dosing solution effectively eliminates sorption of glyburide to administration components.

Example 6

Figure 12:
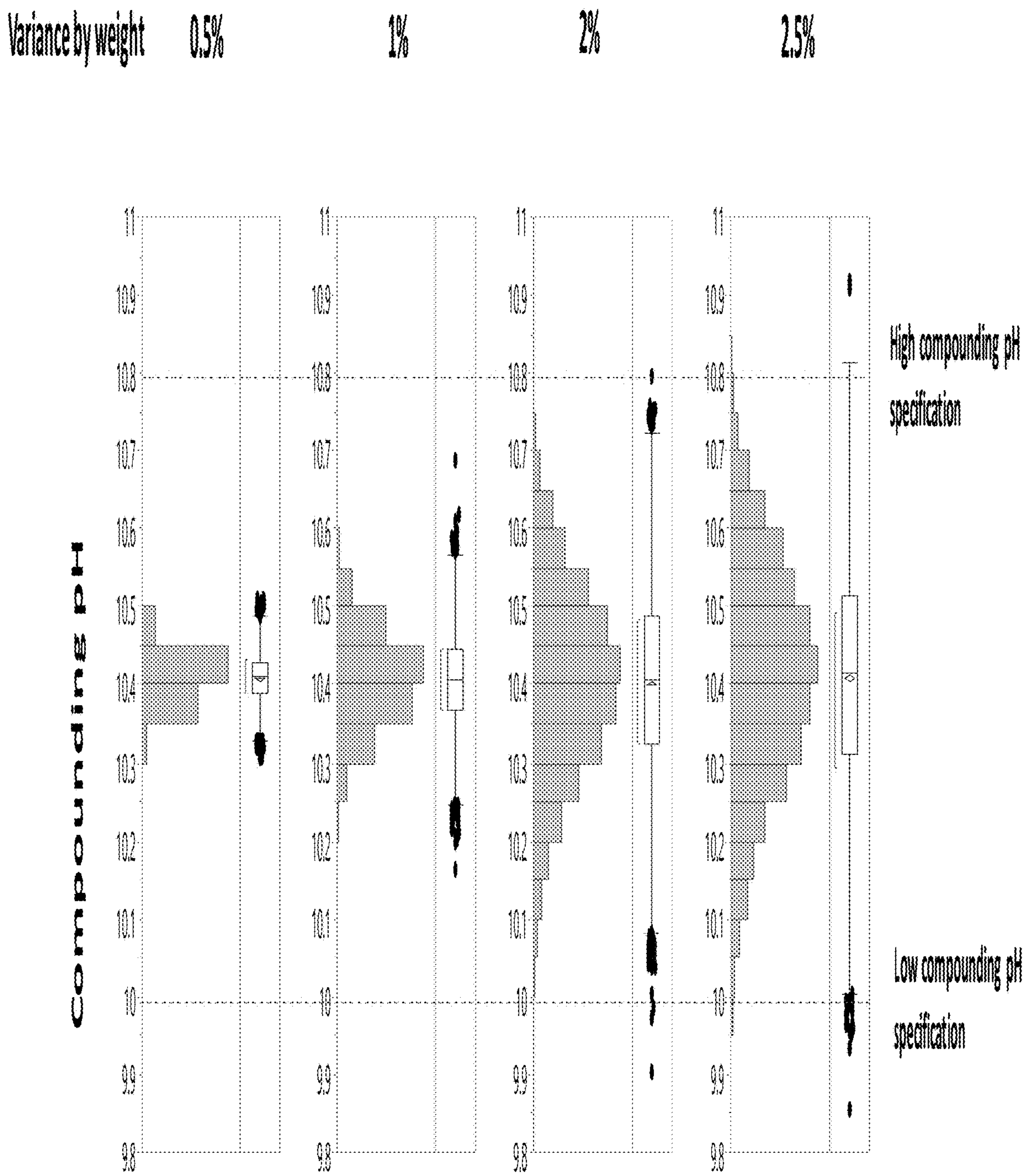
FIG. 12 shows the effect of the weighing variance of TRIS buffer and NaOH on compounding pH. As the variance in the weighing of these components increase, the variance in the compounding pH also increases. A weighing variance of 2% by weight or below results in a range of compounding pH that is still within the target specification range of 10-10.8. However, as the weighing variance increases above 2% by weight, the compounding pH deviates from the target range at the extremes of the variation of weighing of these components.

Further experiments revealed that the compounding pH is strongly dependent on the TRIS concentration, buffer pH, and the base content in the formulation (FIG. 8). Variations in the weighing of buffer and base could potentially cause changes to the expected compounding pH, leading to process variation from batch to batch. An analysis on the effect of weighing inputs, and thus the variation in compounding pH obtained (FIG. 12). A weighing variance of 2% of the TRIS buffer and NaOH would result in a compounding pH distribution that is still within the target specification of 10-10.8 (0.5% of compounding pH variation would fall outside the target range). Weighing variances at 2.5% could lead to compounding pH outside the target specification range, and lead to batch to batch process variation. Or in the case of an extremely high compounding pH (i.e. >10.8), the batch would be discarded since there is no mechanism for decreasing the pH in the compounding process. Thus, by establishing a weighing control of 2% or less of critical formulation components that affect the compounding pH (TRIS-base, TRIS-HCl, 1N NaOH), the compounding pH was controlled within the specified range of 10-10.8.

An additional process control of the compounding pH is through the implementation of a pH adjustment step in the compounding process to achieve the target pH specification of 10.4 (±0.4). The order-of-addition of formulation components that control the compounding pH to maintain bulk solution stability throughout the compounding process was found to be Tris-base, Tris-HCl, and then 1N NaOH. Critically, 1N NaOH is added in two portions. The first portion is to enable glyburide solubility and dissolution, in addition to mitigating the drop in pH after addition of Tris-HCl. The resulting pH after Tris-HCl addition is designed to maintain glyburide solubility (at 1 mg/ml) and be below the target compounding pH of 10.4. A second portion of 1N NaOH is used in a pH adjustment step to achieve the target compounding pH. In some aspects, the order-of-addition of formulation components that control the compounding pH to maintain bulk solution stability throughout the compounding process is water, mannitol, first portion of 1N NaOH, glyburide, Tris-base, Tris-HCl, second portion of 1N NaOH. Taken together, a combination of weighing control of critical formulation components and the compounding process steps (order-of-addition and implementation of pH adjustment steps) is useful for process control parameters that impact drug product critical quality attributes.

Example 7

Figure 13:
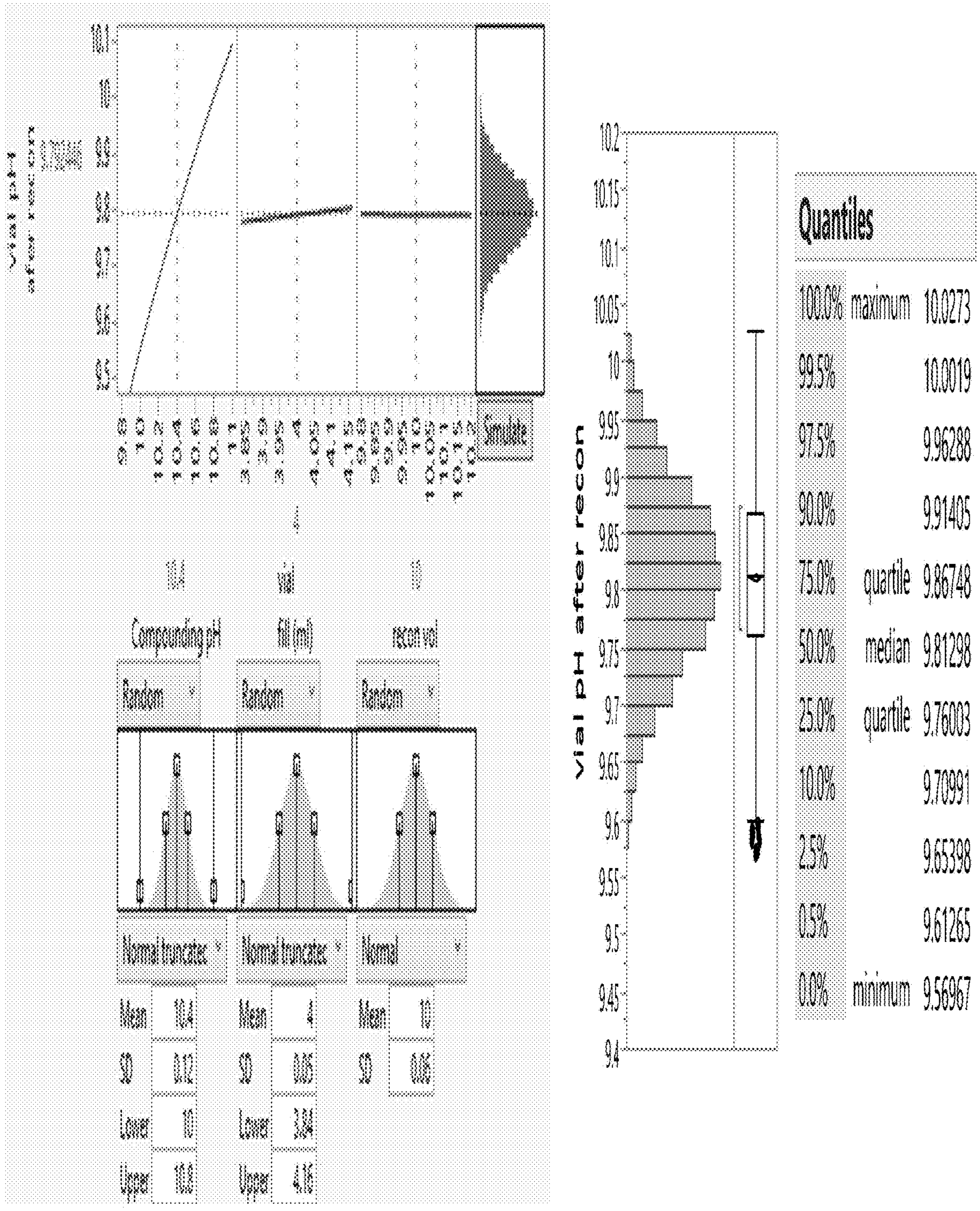
FIG. 13 shows the correlation of reconstitution pH with compounding pH, vial fill, and reconstitution volume based on a non-linear neural network model (training data: $R^2$=0.98; validation data: $R^2$=0.97). (Right) The vial pH after reconstitution is mainly correlated with the compounding pH within the target fill volume and reconstitution volume of interest. The majority of the variance of reconstitution pH is expected to come from the compounding pH (Left).

The compounding pH impacts critical quality attributes of the drug product, including formation of impurities during storage, sorption to administration components, and stability during infusion. A robust process control strategy has been developed for the commercial compounding process to enable control of the compounding parameters. As part of the drug product release testing, the vial pH after reconstitution (10 ml) can be used to ensure that the appropriate compounding pH was achieved during manufacture. The relationship between the compounding pH and vial pH after reconstitution, as well as the expected variation, is shown in FIG. 13. From development studies, it was found that the compounding pH is well correlated with the reconstitution pH. Although vial fill volume also impacts the reconstitution pH, within the target fill volume (4 ml±4%), there is essentially no dependence. Thus, most of the expected variation in reconstitution pH is expected to come from the variation of compounding pH. The target reconstitution pH is 9.8 with a range of 9.5-10.0. In some aspects, the concentration after reconstitution is 0.4 mg/ml (4 mg/10 ml). Adding in a 20% excess in concentration (i.e. 0.4 mg/ml*1.2=0.48 mg/ml) to ensure appropriate stability, it was found that a vial reconstitution pH of at least 9.3 is required (FIG. 5).

The present disclosure provides methods and formulations for addressing the confounding challenges with intravenous glyburide formulations including low solubility, low stability, sorption to administration materials, degradation, drug wastage, and the need to administer large amounts of saline for infusion. Using the described combination of specific base, specific buffer, specific ratio of base to glyburide, and a sugar alcohol, and compounding according to the present disclosure, it was found that the solubility requirements of the final dosing solution are met and can ensure solution stability throughout the entire infusion period. Furthermore, drug sorption to administration components made of PVC or PUR were eliminated, allowing for expanded use of any commonly used medical administration components. To achieve the precise control of the final dosing solution, the disclosed formulation contains the specific buffering agents of the present disclosure in specific amounts described above. The buffering agent, in combination with the appropriate molar ratio of base to glyburide, are critical in process control parameters that impact drug product stability and the solubility and sorption. A compounding pH target of 10.4 (±0.4) was found to be necessary to achieve the critical quality attributes of the drug product. Taken together, the disclosed formulation and process elements provide a robust, stable, and soluble drug product that eliminates the challenges with existing formulations and methods and also provides a method of administering significantly less saline to patients due to decreased drug wastage and increased solubility.

Any of the above protocols or similar variants thereof can be described in various documentation associated with a pharmaceutical product. This documentation can include, without limitation, protocols, statistical analysis plans, investigator brochures, clinical guidelines, medication guides, risk evaluation and mediation programs, prescribing information and other documentation that may be associated with a pharmaceutical product. It is specifically contemplated that such documentation may be physically packaged with an pharmaceutical product according to the present disclosure as a kit, as may be beneficial or as set forth by regulatory authorities.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A lyophilized formulation comprising:

a. glyburide or a pharmaceutically acceptable salt thereof;

b. a buffering agent;

c. a base; and d. a sugar alcohol comprising mannitol, sorbitol, xylitol, or a combination thereof, wherein the formulation has a pH outside of the buffering capacity of the buffering agent when reconstituted in water for injection (WFI), wherein the lyophilized formulation comprises about 70 to 93% (w/w) of the sugar alcohol, and wherein the lyophilized formulation is free of cyclodextrins.

2. The lyophilized formulation of claim 1, wherein the pharmaceutically acceptable salt thereof is a sodium addition salt.

3. The lyophilized formulation of claim 1, wherein the glyburide or pharmaceutically acceptable salt thereof is about 2 to 3.5%, 2.5 to 3.3%, 2.7 to 3.1%, 2.8 to 2.98%, 2.9 to 2.97%, or 2.94 to 2.96% (w/w) of the lyophilized formulation.

4. The lyophilized formulation of claim 1, comprising about 75 to 92%, 80 to 91%, 84 to 90%, 86 to 89%, or 87 to 89% (w/w) of the sugar alcohol.

5. The lyophilized formulation of claim 1, wherein the sugar alcohol is mannitol.

6. The lyophilized formulation of claim 1, comprising the sugar alcohol and the glyburide or pharmaceutically acceptable salt thereof in a weight ratio of 25 to 50:1, 26 to 45:1, 27 to 40:1, 28 to 35:1, 29 to 33:1, 30:1, 31:1, or 32:1.

7. The lyophilized formulation of claim 1, comprising the sugar alcohol and the buffering agent in a weight ratio of 5 to 15:1, 6 to 14:1, 7 to 13:1, 8 to 12:1, 9 to 11:1, 9.5:1, 10:1, or 10.5:1.

8. The lyophilized formulation of claim 1, wherein the base has a pKb of 0.1 to 1.5.

9. The lyophilized formulation of claim 1, wherein the base and the glyburide or pharmaceutically acceptable salt thereof have a molar ratio of 5.0 to 6.7:1, 5.1 to 6.6:1, 5.2 to 6.5:1, 5.3 to 6.4:1, 5.4 to 6.3:1, 5.5 to 6.2:1, 5.6 to 6.1:1, 5.7 to 6.0:1, or 5.2:1, 5.3:1, 5.4:1, 5.5:1, or 5.6:1.

10. The lyophilized formulation of claim 1, wherein the base is NaOH, CaOH, KOH, or a combination thereof.

11. The lyophilized formulation of claim 1, wherein the buffering agent is a Tris, a lysine, an arginine, an ethylenediamine, an imidazole, a 4-(2-Hydroxyethyl) morpholine, a triethanolamine, a glucamine, a deanol (dimethylaminoethanol), or a combination thereof.

12. The lyophilized formulation of claim 1, wherein the buffering agent is a combination of Tris-HCl and Tris-base.

13. The lyophilized formulation of claim 12, having a weight ratio between Tris-HCl and Tris-base of 7:4.

14. The lyophilized formulation of claim 12, having a weight ratio between Tris-HCl and Tris-base of 6.2:5.0.

15. The lyophilized formulation of claim 1, comprising about 5 to 15%, 6 to 14%, 7 to 13%, 8 to 12%, 9 to 13%, or 10 to 12% (w/w) of the buffering agent.

16. The lyophilized formulation of claim 1, reconstituted in 20 mL of water for injection (WFI) and comprising 4 to 60 mM, 5 to 50 mM, 6 to 40 mM, 7 to 30 mM, 8 to 25 mM, 9 to 23 mM, 10 to 21 mM, 11 mM, 12 mM, 13 mM, 14 mM, 15 mM, 16 mM, 17 mM, 18 mM, 19 mM, or 20 mM of the buffering agent.

17. The lyophilized formulation of claim 1, reconstituted in 20 mL of water for injection (WFI) and comprising 1 to 5 mg/ml, 1.2 to 4 mg/ml, 1.5 to 3.5 mg/ml, or 2 to 3 mg/ml of the buffering agent.

18. The formulation of claim 1, wherein the buffering agent has a pKa of 7.7 to 9.2.

19. The lyophilized formulation of claim 1, comprising the base and the glyburide or pharmaceutically acceptable salt thereof in a ratio so the formulation has a pH of 9.8 to 11.2, 9.9 to 11.1, 10.0 to 11.0, 10.1 to 10.9, 10.2 to 10.8, 10.3 to 10.7, or 10.4 to 10.6 when reconstituted in WFI.

20. The lyophilized formulation of claim 1, having a pH of 10 to 11 in 20 mL WFI and a pH of 7.8 to 9 in 500 mL saline infusion solution.

21. A saline infusion solution comprising:

a) glyburide or a pharmaceutically acceptable salt thereof;

b) a buffering agent;

c) a base; and d) a sugar alcohol selected from mannitol, sorbitol, xylitol, or a combination thereof, wherein the saline infusion solution has a glyburide solubility of at least 15 μg/ml and is free of cyclodextrins.

22. The saline infusion solution of claim 21, having a pH of 7.8 to 9, 7.9, 8.0, 8.1, 8.2, 8.3, 8.4, 8.5, 8.6, 8.7, 8.8, or 8.9.

23. The saline infusion solution of claim 21, having a buffer concentration of about 0.1 to 0.5 mM, about 0.15 to 0.4 mM, about 0.2 to 0.3 mM, or about 0.2 mM.

24. The saline infusion solution of claim 21, wherein the pharmaceutically acceptable salt thereof is a sodium addition salt.

25. The saline infusion solution of claim 21, wherein the sugar alcohol is mannitol.

26. The saline infusion solution of claim 21, comprising the sugar alcohol and the glyburide or pharmaceutically acceptable salt thereof in a weight ratio of 25 to 50:1.

27. The saline infusion solution of claim 21, comprising the sugar alcohol and the buffering agent in a weight ratio of 5 to 15:1.

28. The saline infusion solution of claim 21, wherein the buffering agent has a pKa of 7.7 to 9.2.

29. The saline infusion solution of claim 21, wherein the buffering agent is a Tris, a lysine, an arginine, an ethylenediamine, an imidazole, a 4-(2-Hydroxyethyl) morpholine, a triethanolamine, a glucamine, a deanol (dimethylaminoethanol), or a combination thereof.

30. The saline infusion solution of claim 21, wherein the buffering agent is a combination of Tris-HCl and Tris-base.

31. A liquid solution formulation comprising:

a) glyburide or a pharmaceutically acceptable salt thereof;

b) a buffering agent;

c) a base; and d) a sugar alcohol selected from mannitol, sorbitol, xylitol, or a combination thereof, wherein the liquid solution formulation has a pH outside of the buffering capacity of the buffering agent, wherein the liquid solution formulation comprises the sugar alcohol and the buffering agent in a weight ratio of 5 to 15:1, and wherein the liquid solution formulation is free of cyclodextrins.

32. The liquid solution formulation of claim 31, wherein the pharmaceutically acceptable salt thereof is a sodium addition salt.

33. The liquid solution formulation of claim 31, wherein the sugar alcohol is mannitol.

34. The liquid solution formulation of claim 31, comprising the sugar alcohol and the glyburide or pharmaceutically acceptable salt thereof in a weight ratio of 25 to 50:1.

35. The liquid solution formulation of claim 31, comprising the sugar alcohol and the buffering agent in a weight ratio of 5 to 15:1.

36. The liquid solution formulation of claim 31, comprising 20 to 40 mg/ml of the sugar alcohol.

37. The liquid solution formulation of claim 31, wherein the buffering agent has a pKa of 7.7 to 9.2.

38. The liquid solution formulation of claim 31, wherein the base has a pKb of 0.1 to 1.5.

39. The liquid solution formulation of claim 31, wherein the base and the glyburide or pharmaceutically acceptable salt thereof have a molar ratio of 5.0 to 6.7:1.

40. The liquid solution formulation of claim 31, wherein the base is NaOH, CaOH, KOH, or a combination thereof.

41. The liquid solution formulation of claim 31, wherein the buffering agent is a Tris, a lysine, an arginine, an ethylenediamine, an imidazole, a 4-(2-Hydroxyethyl) morpholine, a triethanolamine, a glucamine, a deanol (dimethylaminoethanol), or a combination thereof.

42. The liquid solution formulation of claim 31, wherein the buffering agent is a combination of Tris-HCl and Tris-base.

43. The liquid solution formulation of claim 42, having a weight ratio between Tris-HCl and Tris-base of 7:4.

44. The liquid solution formulation of claim 42, having a weight ratio between Tris-HCl and Tris-base of 6.2:5.0.

45. The liquid solution formulation of claim 31, wherein the buffering agent is a buffer having a pH of 7.8 to 9.

46. The liquid solution formulation of claim 31, comprising the base and the glyburide or pharmaceutically acceptable salt thereof in a ratio so the liquid solution formulation has a pH of 9.8 to 11.2.

47. The liquid solution formulation of claim 31, having an osmolarity of about 250 to 350 milliOsmoles/liter (mOsm).

48. The liquid solution formulation of claim 31, having a glyburide solubility of at least 15 μg/ml in a saline infusion solution.

49. The liquid solution formulation of claim 31, having a pH of 7.8 to 9 in a saline infusion solution.

50. The liquid solution formulation of claim 31, having a buffer concentration of about 0.1 to 0.5 mM in a saline infusion solution.

51. The liquid solution formulation of claim 31, having a pH of 10 to 11.

* * * * *